(12) United States Patent
Zheng et al.

(10) Patent No.: US 9,073,857 B2
(45) Date of Patent: Jul. 7, 2015

(54) ARIPIPRAZOLE TYPE I MICROCRYSTAL, ARIPIPRAZOLE SOLID PREPARATIONS, AND PREPARATION METHOD

(75) Inventors: Siji Zheng, Shanghai (CN); Bo Tan, Shanghai (CN); Linyong Fu, Shanghai (CN); Xiaoyi Liu, Shanghai (CN); Shaoqing Yuan, Shanghai (CN); Zhihui Cao, Shanghai (CN)

(73) Assignees: SHANGHAI ZHONGXI PHARMACEUTICAL CORPORATION, Shanghai (CN); SHANGHAI ZHONGXI SUNVE PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 14/129,838

(22) PCT Filed: Jun. 26, 2012

(86) PCT No.: PCT/CN2012/077515
§ 371 (c)(1),
(2), (4) Date: Dec. 27, 2013

(87) PCT Pub. No.: WO2013/000392
PCT Pub. Date: Jan. 3, 2013

(65) Prior Publication Data
US 2014/0135344 A1 May 15, 2014

(30) Foreign Application Priority Data
Jun. 27, 2011 (CN) .......................... 2011 1 0180032

(51) Int. Cl.
| | |
|---|---|
| *C07D 215/227* | (2006.01) |
| *A61K 9/00* | (2006.01) |
| *A61K 9/20* | (2006.01) |
| *A61K 9/48* | (2006.01) |
| *A61K 31/496* | (2006.01) |

(52) U.S. Cl.
CPC .......... *C07D 215/227* (2013.01); *A61K 9/0056* (2013.01); *A61K 9/2018* (2013.01); *A61K 9/2031* (2013.01); *A61K 9/2054* (2013.01); *A61K 9/4858* (2013.01); *A61K 9/4866* (2013.01); *A61K 31/496* (2013.01)

(58) Field of Classification Search
None
See application file for complete search history.

(56) References Cited

U.S. PATENT DOCUMENTS 7,504,504 B2 * 3/2009 Aronhime et al. ............ 544/363

FOREIGN PATENT DOCUMENTS

| CN | 1871007 A | 11/2006 |
|---|---|---|
| CN | 101066267 A | 11/2007 |
| CN | 101172966 A | 5/2008 |
| CN | 101351193 A | 1/2009 |
| CN | 102850268 A | 1/2013 |
| GB | 2 505 859 A | 3/2014 |
| WO | WO 2005/041970 A1 | 5/2005 |
| WO | WO 2007/081367 A1 | 7/2007 |

OTHER PUBLICATIONS

Khan et al. in Basic Principles of Forensic Chemistry, Chapter 8, pp. 91-97, Humana press Publishers, 2012 Edition.*
Aug. 7, 2014 Office Action issued in Chinese Patent Application No. 201110180032.0 w/translation.
IL 230190 Israeli International Stage Application of PCT/CN2012/077515 filed Dec. 26, 2013 submitted under Zheng, Siji.
Oct. 18, 2012 translation of Written Opinion issued in International Application No. PCT/CN2012/077515.
Dec. 11, 2013 Chinese Office Action issued in Chinese Application No. 201110180032.0 (with translation).
Oct. 18, 2012 International Search Report issued in International Application No. PCT/CN2012/077515.
Dec. 29, 2014 Office Action issued in Chinese Application No. 201110180032.0.

* cited by examiner

*Primary Examiner* — Emily Bernhardt
(74) *Attorney, Agent, or Firm* — Oliff PLC

(57) ABSTRACT

A method for preparing an aripiprazole type I microcrystal, including the following steps: dissolving aripiprazole in an acidifier, acquiring a medicament-having acid solution; adding an alkalizer while stirring, then adding water or aqueous ethanol 10 to 60 wt % while stirring, and separating by precipitation the aripiprazole type I microcrystal. Furthermore, a method for preparing a solid preparation having the aripiprazole type I microcrystal, an aripiprazole microcrystal having an average particle size of less than 20 μm, and a solid preparation having the microcrystal. The method for preparing the aripiprazole type I microcrystal allows reduced pollution and loss, great safety, easy and convenient, reduced use of organic solvents, obviated need for demanding process conditions (such as cooling condition) and apparatus, low cost, and facilitated applicability in industrialized manufacturing. This solid preparation provides great stability, solubility, and bioavailability, reduced individual differences, and reduced content of related substances.

26 Claims, 5 Drawing Sheets

ARIPIPRAZOLE TYPE I MICROCRYSTAL, ARIPIPRAZOLE SOLID PREPARATIONS, AND PREPARATION METHOD

FIELD OF INVENTION

The present invention relates to a preparation method of aripiprazole type I microcrystal, a preparation method of aripiprazole solid preparation, and an aripiprazole type I microcrystals and an aripiprazole solid preparations having the microcrystal.

PRIOR ARTS

Aripiprazole, the chemical name of 7-[4-[4-(2,3-dichlorophenyl)-1-piperazinyl]butoxy]-3,4-dihydro-2(1H)-quinolinone, molecular weight 448.39, belongs to the quinolinone derivatives, approved for marketing by the U.S. FDA in November 2002 for the treatment of schizophrenia.

Aripiprazole is an insoluble drug. When it is made into oral preparation such as tablet or other solid preparations containing the quick soluble formula, its particle size has a larger effect on its active bioavailability. The dissolution rate of aripiprazole type I crystal disclosed at the Japan and South Korea Analytical Chemistry Annual Meeting in 1998 is less than 70% within 45 minutes, and the bioavailability is relatively low. If the aripiprazole is crushed by the universal grinder through mechanical pulverization treatment, the average particle size generally only reaches about 100 micron, and the dissolution characteristic of the obtained solid preparation is not ideal. In addition, the process of mechanical pulverization has problems of dust, environmental pollution, and great loss and so on. Moreover, the drug activity of aripiprazole is relatively high, so the inhalation of aripiprazole dust can easily cause problem of adverse drug reaction of operators. Therefore, it is necessary to research aripiprazole type I crystal with particle size no more than 100 micron, and the preparation method which can avoid the above defects of the mechanical pulverization method.

Chinese patent application (Publication No. CN1871007A) discloses a method with an impinging jet crystallization process for preparing sterile and particulate aripiprazole hydrate crystal with average particle size of less than 100 micron, and the aripiprazole hydrate crystal produced by this method can be used to prepare sterile and freeze-dried aripiprazole pharmaceutics and aripiprazole injectable aqueous suspension formulations, Chinese patent application (Publication No. CN101172966A) discloses a method for preparing aripiprazole type I microcrystal, in which crude product of aripiprazole with about 10-fold amount of ethanol were heated under reflux until dissolved, then low-temperature water was added under stirring with the temperature quickly decreasing, the precipitated crystal was filtrated, washed and then dried.

However, the above methods are complicated and high-cost. Therefore, there is an urgent need to seek a method to prepare the aripiprazole microcrystal and solid preparation which allows for easy and convenient operation, great safety, and can guarantee various excellent product properties.

CONTENT OF THE PRESENT INVENTION

The technical problem to be solved in the present invention is to overcome the defects in the mechanical pulverization method of preparing aripiprazole microcrystal that the average particle size of crystal only reaches about 100 micron, and the method will result in environmental pollution, great loss, serious security risks, and to overcome the defects in the other existing methods that the operate is relatively complicated and the cost is high, and the present invention provides aripiprazole type I microcrystal with average particle size of no more than 50 micron, a preparation method which has reduced pollution and loss, great safety, easy and convenient operation and low cost, and can obtain aripiprazole type I microcrystal with average particle size of no more than 50 micron, and also a aripiprazole solid preparation with excellent stability, especially crystal stability, good dissolution property, low content of related substances and a preparation method thereof.

In order to solve the above technical problems, the inventor found a new path that uniquely uses "Acid-Base Solventing-out Crystallization Method" or "Acid-Base Solventing-out Carrier Dispersion Crystallization Method" to prepare aripiprazole type I microcrystal. Specifically, the present invention relates to the following technical solutions:

The present invention relates to a method for preparing aripiprazole type I microcrystal, which includes the following steps: dissolving aripiprazole in an acidic solution having an acidifier, acquiring a medicament-having acid solution; then adding an alkalizer while stirring, then adding water or aqueous ethanol of 10 to 60 wt % while stirring, and separating the precipitated aripiprazole type I microcrystal.

In the present invention, raw materials of the said aripiprazole can be in a variety of crystalline forms of aripiprazole prepared by the existing method, such as aripiprazole type I crystal, or type II crystal, as well as amorphous aripiprazole.

In the present invention, the said acidifier refers to an acid reagent that can make the aripiprazole completely dissolved in the acidic solution having the acidifier. According to the common knowledge in the field, the said acidifier should be a reagent which is pharmaceutically acceptable and has compatibility with the aripiprazole. In the present invention, the said compatibility means coexistence without adverse effects. The said acidifier can be a single acidifying agent as well as composite acidifying agents consisting of no less than two components, which is preferably selected from one or more among hydrochloric acid, lactic acid, and malic acid, more preferably is hydrochloric acid. The dosage of the said acidifier is at least the minimum dosage which can completely dissolve the aripiprazole, preferably 1~1.2 times over the minimum dosage, more preferably 1~1.05 times over the minimum dosage. The said minimum dosage refers to the minimum amount of a certain acidifier that can make the aripiprazole completely dissolved under the preparation conditions of the same solvent and medicament-having acid solution. The said minimum dosage can be obtained by simple conventional method: under the preparation conditions of the same solvent and medicament-having acid solution, the minimum dosage is obtained when aripiprazole is just dissolved by gradually increasing a certain acidifier's dosage. Based on experiments, when the acidifier is hydrochloric acid, the molar ratio of the hydrochloric acid to the aripiprazole is generally 0.8~1.2, preferably 0.9~1.1, more preferably 0.95~1.05. When the acidifier is lactic acid, the molar ratio of the lactic acid to the aripiprazole is generally 1.8~2.5, preferably 2~2.1.

In the invention, the solvent of the said acidic solution having an acidifier can be organic solvent, or the mixture of water and organic solvent, preferably the mixture of water and organic solvent The said organic solvent is selected from the acceptable solvents in the pharmaceutical field according to the principle that the solubility of the aripiprazole in this organic solvent is better than that in water, and the water-miscible organic solvent is preferred, such as conventionally used water-soluble alcohols in the pharmaceutical field, like one or more selected from ethanol, propylene glycol, glycerol, ethylene glycol, isopropanol and benzyl alcohol etc., preferably ethanol. The dosage of the organic solvent can be selected optionally in the mixture of water and the organic solvent, preferably is the concentration of no less than 40% mass percentage, more preferably the concentration of no less than 80%, in order to obtain the aripiprazole type I microcrystal with smaller particle size. When using the aqueous ethanol solution, the concentration of ethanol is preferably no less than 40% mass percentages, more preferably no less than 80%. The solvent dosage in the said acidic solution having an acidifier can make the aripiprazole completely dissolved in the acidifier-containing acid solution at least, generally is no less than twice the mass of aripiprazole, preferably 3 to 5 times.

Before adding the alkalizer, some adjuvants can be added, such as one or more among surfactant, solubilizer and the water-soluble carrier and so on, and then the alkalizer can be added. These adjuvants can be added during the preparation of the medicament-having acid solution or after the preparation of the medicament-having acid solution, and the order of the addition is related to the mutual solubility of the adjuvant and the said medicament-having acid solution. For the adjuvant which is mutually soluble with the medicament-having acid solution, in other words, which can keep the medicament-having acid solution in the solution state, and not in the turbid liquid state or the viscous liquid state, the adjuvant can be added during the preparation of the medicament-having acid solution or after the preparation of the medicament-having acid solution. For the adjuvant which is immiscible with the medicament-having acid solution, in other words, which can make the medicament-having acid solution change from the solution state into the turbid liquid state or the viscous liquid state, the adjuvant should be added usually after the preparation of the medicament-having acid solution. Generally speaking, the said surfactant and/or solubilizer can be added during the preparation of the medicament-having acid solution or after the preparation of the medicament-having acid solution; the said water-soluble carrier and/or disintegrant should be added after the preparation of the medicament-having acid solution, except the water-soluble carrier (such as polyethylene glycol and hydroxypropyl β cyclodextrin) that is soluble in the medicament-having acid solution. If the said water-soluble carrier is added during the preparation of the medicament-having acid solution, the dosage of the water-soluble carrier should be controlled no more than the dosage which can ensure the aripiprazole completely dissolved in the acidic solution having an acidifier. This moment, after adding the said dosage of the water-soluble carrier, the water-soluble carrier can be added into again. When the dosage is larger, the mixture of the acquired medicament-having acid solution and the adjuvant would be in the form of turbid liquid or viscous liquid. In the present invention, the added surfactant and/or solubilizer is preferably selected from one or more among povidone, sodium lauryl sulfate, poloxamer, polyoxyethylene castor oil, Tween-80 and polyoxyl 40 stearate, more preferably from one or more among povidone, sodium lauryl sulfate, poloxamers, and Tween-80. In the present invention, the added water-soluble carrier are preferably selected from one or more among lactose, mannitol, sucrose, polyethylene glycol (preferably polyethylene glycol 400-8000), hydroxypropyl β cyclodextrin and maltitol, more preferably one or more among lactose, mannitol, polyethylene glycol 6000, hydroxypropyl β cyclodextrin and sucrose. The dosage of the said surfactant and/or solubilizer is preferably 0.01~2 times the mass of aripiprazole, more preferably 0.8~1.2 times. The dosage of the said water-soluble carrier is preferably 1~5 times the mass of the aripiprazol, more preferably 2.5~3.5 times. According to the above procedure to add surfactant and/or solubilizer, it can increase the solubility of the aripiprazole in the acid solution and reduce the solvent dosage so as to benefit the operation of subsequent steps. It is especially worth mentioning that, it can make the dissolution performance of the aripiprazole better, when adding one or more among surfactant, solubilizer and water-soluble carrier according to the above procedure, especially water-soluble carrier.

Preferably, in the preparation of the medicament-having acid solution, it can appropriately increase the temperature through the heating method (such as hot water-bath), so as to benefit the dissolution of the aripiprazole, and the temperature generally increases to 30~85° C. When the solvent is aqueous ethanol, it preferably increases to 30~70° C., more preferably to 40~60° C.

In the present invention, the said alkalizer refers to the reagent which can reduce the acidity of the mixture of the alkalizer and the medicament-having acid solution relative to the acidity of the medicament-having acid solution, for example, inorganic strong alkali (such as sodium hydroxide or potassium hydroxide), strong alkali and weak acid salt (such as inorganic strong alkali and weak acid salt, for example, sodium carbonate, potassium carbonate, disodium hydrogen phosphate). The said alkalizer can be a single alkalizer, as well as composite alkalizer consisting of no less than two ingredients, most preferably sodium hydroxide or sodium carbonate. According to the conventional knowledge in this field, the said alkalizer should be the reagent which is pharmaceutically acceptable and compatible with the aripiprazole. The dosage of the said alkalizer is at least the one that can reduce the acidity of the mixture of the alkalizer and the medicament-having acid solution relative to that of the medicament-having acid solution. In order to prevent the locally dramatic increasing of the pH value of the system after adding the said alkalizer, the said alkalizer such as sodium hydroxide is preferably added in the form of a solution, and the said alkalizer such as sodium carbonate is added in the form of a solution or after being uniformly distributed in other adjuvant. The concentration of the said alkalizer in the alkalizer-having solution is preferably 5~20 wt %. The said solution is preferably water solution.

The invention especially prefers the following types of groups of acidifier and alkalizer the said acidifier is hydrochloric acid, and the said alkalizer is sodium hydroxide, and the molar ratio of sodium hydroxide to hydrochloric acid is preferably 0.95~1.2, more preferably is 0.99~1.1; the said acidifier is hydrochloric acid, and the said alkalizer is sodium carbonate, and the molar ratio of sodium carbonate to hydrochloric acid is preferably 0.95~1.2, more preferably is 0.99~1.1; or the said acidifier is hydrochloric acid, and the said alkalizer is sodium hydroxide and sodium carbonate, and the molar ratio of the mole sum of sodium hydroxide and sodium carbonate to hydrochloric acid is preferably 0.95~1.2, more preferably is 0.99~1.1.

In the present invention, the said alkalizer can be added once, or can be divided into no less than two parts to add. For the speed of the adding, the said alkalizer can be directly and fast poured or dropped. The present invention prefers the way of all-in dropwise, and the dropping speed is preferably to finish the dropping within 0.5~2 minutes. After adding the alkalizer, it is preferred that after 2~10 minutes stirring the water or aqueous ethanol of 10 to 60 wt % is added under stirring.

In the present invention, there is no special requirement for the dosage of the said water or 10~60 wt % aqueous ethanol solution, and it is generally no less than twice of the mass of the medicament-having acid solution, preferably 3~10 times of the mass of the medicament-having acid solution. After adding the water or aqueous ethanol of 10 to 60 wt %, it is preferred to obtain the mixture solution after 2~5 minutes stirring. After this step, and also before separating the precipitated aripiprazole type I microcrystal, the mixture solution obtained in this step can be processed by a dispersion treatment by using colloid mill or homogenizer as needed, to further reduce the particle size of the aripiprazole.

In the present invention, the said separating the precipitated aripiprazole type microcrystal can be separated according to the conventional methods in the art which generally include suction filtration, washing and suction filtration, drying. The said washing can be performed by using water or aqueous ethanol of 10 to 60 wt %, and the dosage of the water or aqueous ethanol of 10 to 60 wt % is preferably 1~5 times the mass of aripiprazole every time. The number of washing and suction filtration is generally 1~3 times. The said drying can be performed by the conventional methods in the art, such as static drying or dynamic drying. Wherein, the said static drying, for example, can be performed at 40~100° C. (preferably 60~70° C.) with decompression for 3~8 hours (preferably 5~6 hours), and the vacuum pressure of decompression is preferably 450 mmHg~76 mmHg, more preferably 150 mmHg. The said dynamic drying, for example, can be performed at 50~80° C. (preferably 60~70° C.) in double cone vacuo drying mixer for 2~6 hours (preferably 3~5 hours).

In the present invention, the speed of the said stirring condition is one at which the system can mix homogeneously at least, more preferably a stirrer's linear speed of 150~500 m/min.

In a preferred embodiment of the present invention, in order to prepare the aripiprazole type I microcrystal with average particle size of no more than 20 micron, the specific steps are:

In a preferred embodiment of the present invention, the preparation of the said aripiprazole type I microcrystal is carried out as follow; dissolve the aripiprazole type I microcrystal into an aqueous ethanol solution containing hydrochloric acid, acquire a medicament-having acid solution; then add the solution of sodium hydroxide and/or sodium carbonate under stirring, and after stirring for 2~10 minutes add water under stirring, and after stirring again for 2 to 5 minutes, separate the precipitated aripiprazole type I microcrystal; wherein the concentration of ethanol in aqueous ethanol solution was no less than 95 wt %; when the alkalizer is sodium hydroxide, the molar ratio of sodium hydroxide to hydrochloric acid is 0.95~1.0; when the alkalizer is sodium carbonate, the molar ratio of sodium carbonate to hydrochloric acid is 0.9~1.0; when the alkalizer is sodium hydroxide and sodium carbonate, the molar ratio of sodium hydroxide to hydrochloric acid is 0.85~0.9, and the molar ratio of sodium carbonate to hydrochloric acid is 0.11~0.13; the said stirring speed is preferably 150~500 m/min.

Wherein, the molar ratio of hydrochloric acid to aripiprazole is 1.0~1.1; the dosage of the said aqueous ethanol solution is preferably 2.5~3.5 times the mass of aripiprazole, and the methods of adding the said aqueous solution of the alkalizer is preferably direct pouring, or dropping within 0.5~2 minutes; the concentration of the said aqueous solution of the alkalizer is preferably 5~15 wt %; the dosage of water is preferably 2~4 times the mass of the medicament-having acid solution. Preferably, before adding the alkalizer, one or more among surfactant, solubilizer and the water-soluble carrier can be added, and the said surfactant and/or solubilizer is preferably povidone, and the said water-soluble carrier is preferably lactose and/or mannitol. The dosage of the said water-soluble carriers is preferably 2.5~3.5 times the mass of aripiprazole, and the dosage of the said surfactant and/or solubilizer is preferably 0.8~1.2 times the mass of aripiprazole. The said separation method is suction filtration, and the crystal obtained after the suction filtration is preferably washed by water or 30~60 wt % aqueous ethanol solution and filtered through suction filtration 2~3 times, and the dosage of water or 30~60 wt % aqueous ethanol solution is preferably 1~5 times the mass of input aripiprazole. Preferably, before separation, the dispersion treatment is performed by using homogenizer or colloid mill for no less than 10 minutes.

The present invention also relates to a kind of aripiprazole type I microcrystal with average particle size of less than 20 micron.

Wherein, the aripiprazole type I microcrystals is prepared by the above-mentioned preparation method through which can prepare the aripiprazole type I microcrystal with average particle size of less than 20 micron.

The present invention also relates to a preparation method of aripiprazole solid preparations, including the following steps: (1) prepare the aripiprazole type I microcrystal through the above-mentioned preparation method; (2) use the aripiprazole type I microcrystal and adjuvants to prepare aripiprazole tablet or capsule by dry preparation method.

Wherein, the average particle size of the said aripiprazole type I microcrystal is preferably no more than 50 micron, more preferably no more than 20 micron.

In this invention, the said dry method can be carried out by conventional dry method in the pharmaceutical field, generally including: after mixing the aripiprazole type I microcrystal and adjuvants homogeneously, directly add them into capsule to obtain the capsule, or press powder into tablet through direct compression method to obtain the tablet, or through a hot melting granulation process to make granules, then add them into capsule or press them into tablet to obtain the capsule or tablet. The present inventors have found that, the main factors that affect the content of the related substances in aripiprazole solid preparation include: (1) the aripiprazole solvate is formed during the preparation process of the preparation, due to solvent contact; and (2) because of the friction, collision and extrusion during the preparation process of the preparation, the crystal form of aripiprazole type I microcrystal is changed, and the stability of aripiprazole type I microcrystal decreases. Therefore, this invention prefers the dry method, in order to avoid the contact with various solvents during the preparation process, and particularly prefers the method that after mixing the aripiprazole type I microcrystal and adjuvants homogeneously, directly add them into capsule to obtain the capsule.

After mixing the aripiprazole type I microcrystal and adjuvants homogeneously by dry method, when adding them into capsule to obtain capsule preparation, the said adjuvants include filler, disintegrant and lubricant. The said filler is the conventional filler of such agents in the art, preferably one or more among lactose, anhydrous lactose, mannitol, microcrystalline cellulose, starch, xylitol, pregelatinized starch and maltitol, more preferably one or more among lactose, anhydrous lactose, mannitol, microcrystalline cellulose, starch, and pregelatinized starch. The said disintegrant is the conventional disintegrant of such agents in the art, preferably one or more among sodium carboxymethyl starch, hydroxypropyl cellulose, cross-linked polyvinyl pyrrolidone and cross-linked sodium carboxymethylcellulose. The said lubricant is the conventional lubricant of such agents in the art, preferably one or more among colloidal silica, sodium stearyl fumarate, talc and magnesium stearate. The sum of the dosage of the said filler and the water-soluble carrier, is generally 70~95% the mass of content material in the capsule, preferably 80~90%; the dosage of the said disintegrant is preferably 2~8% the mass of content material in the capsule; the dosage of the said lubricant is preferably 0.5~4% the mass of content material in the capsule.

When preparing the aripiprazole tablet by the direct compression process, it can use the adjuvants of the direct compression process in the art and it can follow the routine steps. The said adjuvants include direct compression adjuvant, disintegrant and lubricant. The said direct compression adjuvant generally includes one or more among a variety of direct compression lactose, direct compression mannitol, direct compression microcrystalline cellulose and direct compression complexes, and the said direct compression lactose is preferably anhydrous direct compression lactose (DT) and/or rapid flow direct compression anhydrous lactose (DTHV) of the Kerry Company in the USA and so on. The said direct compression mannitol is preferably the PEARLITOL® (mannitol) of Roquette Company in France. The said direct compression microcrystalline cellulose is preferably one or more among microcrystalline cellulose series AVICEL® PH-102NF, AVICEL® PH-102SCG* and AVICEL PH-200NF of FMC company in USA. The said direct compression complexes is preferably one or more among Ludipress® (from the pharmaceutical lactose, PVP K30, PVPP through physical mixture), Ludipress® LCE (from the mixture of pharmaceutical lactose and PVP K30), Ludiflash® (from the mannitol, PVP K30, PVPP through physical mixture) of BASF Company, Cellactose® 80 (the lactose and powdered cellulose composites), MicroceLac100 (lactose and microcrystalline cellulose composites) and StarLac (lactose and starch composites) of MEGGLE company in Germany. The said disintegrant is the conventional disintegrant of such agents in the art, preferably one or more among sodium carboxymethyl starch, hydroxypropyl cellulose, cross-linked polyvinyl pyrrolidone and cross-linked sodium carboxymethylcellulose. The said lubricant is the conventional lubricant of such agents in the art, preferably one or more among colloidal silica, sodium stearyl fumarate, talcand magnesium stearate. The dosage of the said direct compression adjuvant can be selected in conventional amount, and the sum of the dosage of the said water-soluble carrier and the said direct compression adjuvant is generally 80~98% the mass of the said tablet, preferably 90~95%; the dosage of the said disintegrant can be selected in conventional amount, preferably 2~5% the mass of the said tablet, and the dosage of the said lubricant can be selected in conventional amount, preferably 0.5~3% the mass of the said tablet.

When preparing the aripiprazole tablet and capsule by the hot melting granulation method, the said adjuvants include filler, disintegrant and lubricant and the pharmaceutically acceptable water-soluble hot-melt material, and the said water-soluble hot-melt material is the pharmaceutically acceptable water-soluble material which is in the solid form at the temperature of 18~26° C. and is capable of being softened or melted by heat. The said filler is the conventional filler of such agents in the art, preferably one or more among lactose, anhydrous lactose, mannitol, microcrystalline cellulose, starch, xylitol, pregelatinized starch and maltitol, more preferably one or more among lactose, anhydrous lactose, mannitol, microcrystalline cellulose, starch, and pregelatinized starch. The said disintegrant is the conventional disintegrant of such agents in the art, preferably one or more among sodium carboxymethyl starch, hydroxypropyl cellulose, cross-linked polyvinyl pyrrolidone and cross-linked sodium carboxymethylcellulose. The said lubricant is the conventional lubricant of such agents in the art, preferably one or more among colloidal silica, sodium stearyl fumarate, talc and magnesium stearate. The softening or melting temperature of the said water-soluble hot-melt material is preferably 40~65° C. On one hand, the said water-soluble hot-melt material in this invention has special softening or melting temperature, producing an adhesive force after melting, on the other hand, it is solid at room temperature so as to meet the need for hot melting granulation. The said water-soluble hot-melt material is preferably one or more among polyethylene glycol (PEG), poloxamers oxide and polyoxyl 40 stearate. The said polyethylene glycol is preferably any one or a few among polyethylene glycol 4000-10000, preferably polyethylene glycol 6000 in this invention. The dosage of the said water-soluble hot-melt material is preferably 8%~25% the mass of the said tablet or the content material of the capsule, more preferably 10%~18%. The sum of the dosage of the said filler and the said water-soluble carrier is generally 60%~90% the mass of the said tablet or the content material of the capsule, preferably 70%~80%; the dosage of the said disintegrant is preferably 2%~5% the mass of the said tablet or the content material of the capsule; the dosage of the said lubricant is preferably 0.5%~3% the mass of the said tablet or the content material of the capsule.

According to the need, when preparing the aripiprazole preparation by the various methods mentioned above, other adjuvant can be used in the process, such as one or more among povidone, hydroxypropyl methyl cellulose, sodium lauryl sulfate, poloxamer, polyoxyethylated castor oil and Tween-80, and the dosage is preferably no more than 3% the mass of the said tablet or the content material of the capsule. The said other adjuvant also can include antioxidant. The said antioxidant can be selected in accordance with the common knowledge in the art, preferably from one or more among sodium metabisulfite, sodium bisulfite, sodium sulfite, sodium thiosulfate, L-cysteine, sodium L-ascorbate and vitamin C, most preferably sodium bisulfite and/or L-cysteine as the selected antioxidant. The dosage of the said antioxidant can be selected in conventional amounts, preferably 0.1%~10% the mass of aripiprazole, more preferably 1%~5% the mass of aripiprazole.

In a preferred embodiment of the present invention, when producing the capsule by directly filling the capsule, the said adjuvants include 80~95% of filler, 1~7% of disintegrant, 0.5~3% of lubricant and 0~2% povidone. Wherein, the said filler is preferably one or more among lactose, anhydrous lactose, microcrystalline cellulose, starch, mannitol and pregelatinized starch, more preferably the combination of lactose, microcrystalline cellulose and starch, or the combination of mannitol and microcrystalline cellulose, or the combination of lactose and starch, or the combination of lactose, pregelatinized starch and starch, or the combination of anhydrous lactose, microcrystalline cellulose and starch. The said disintegrant is preferably one or more among sodium carboxymethyl starch, cross-linked polyvinyl pyrrolidone and hydroxypropyl cellulose. The said lubricant is preferably one or more among colloidal silica, magnesium stearate and talc. The said adjuvants also include 1~2% of antioxidant, and the said antioxidant is preferably sodium bisulfite, and the percentage is the relative percentage of the mass of aripiprazole.

In a preferred embodiment of the present invention, when producing the aripiprazole tablet by the direct compression technology, the said adjuvants include 85~90% of the direct compression adjuvant, 2~5% of disintegrant, 0.5~2% of lubricant and 0~2% povidone. Wherein, the said direct compression adjuvant is preferably one or more among the direct compression lactose, the direct compression mannitol, microcrystalline cellulose and composite lactose. The said disintegrant is preferably one or more among sodium carboxymethyl starch, cross-linked polyvinyl pyrrolidone and crosslinked sodium carboxymethyl cellulose. The said lubricant is preferably one or more among colloidal silica, magnesium stearate and talc. The said adjuvants also include 1~2% of antioxidant, and the said antioxidant is preferably sodium bisulfite, and the percentage is the relative percentage of the mass of aripiprazole.

In a preferred embodiment of the present invention, when producing the aripiprazole tablet and capsule by the hot melting granulation method, the said adjuvants include 65~80% of filler, 9~20% of the water-soluble hot-melt material, 2~5% of disintegrant, 0.5~3% of lubricants and 0~2% povidone. Wherein, the said filler is preferably one or more among lactose, microcrystalline cellulose and starch. The said water-soluble hot-melt material is preferably polyethylene glycol 6000. The said disintegrant is preferably sodium carboxymethyl starch and/or crosslinked polyvinyl pyrrolidone. The said lubricant is preferably one or more among colloidal silica, magnesium stearate and talc. The said adjuvants also include 1~3% of antioxidant, and the said antioxidant is preferably one or more among sodium sulfite, sodium bisulfite or L-cysteine, and the percentage is the relative percentage of the mass of aripiprazole.

In the aripiprazole solid preparation of the present invention, the aripiprazole content is generally 1~30 mg, preferably 5 mg, 10 mg, 20 mg and 30 mg. The percentage by mass of the aripiprazole in the solid preparation is generally 2%~30%, preferably 5%~20%.

The present invention further relates to the aripiprazole solid preparations that contain the aripiprazole type I microcrystal with average particle size of less than 20 micron.

Wherein, the above-mentioned aripiprazole solid preparation is prepared by the above-mentioned preparation methods of the aripiprazole solid preparation, in which the step (1) is the above-mentioned method that can prepare the aripiprazole type I microcrystal with particle size of less than 20 micron.

In the present invention, the above-mentioned preferred conditions can be used in any combination on the basis of the common knowledge in the art, to obtain each preferred embodiments of the present invention.

In the present invention, the used reagents and raw materials are all commercially available.

The effects of the positive progress in the present invention include:

1. The preparation method of preparing aripiprazole type I microcrystal of the present invention allows for reduced pollution and loss, great safety, easy and convenient operation, reduced use of organic solvent, obviated need for demanding process conditions (such as cooling condition) and apparatus, low cost, facilitated applicability in industrialized manufacturing, and is able to prepare the aripiprazole type I microcrystal with average particle size (D[4,3]) no more than 50 micron.

2. The aripiprazole solid preparation prepared by the preparation method of solid preparation of the present invention is provided with great stability, solubility, and bioavailability, reduced individual differences, and reduced content of related substances. In particular, the preferred preparation method of solid preparations in the present invention adopts dry preparation method and fill the capsule directly, and can effectively prevent the forming of the aripiprazole solvate and the changing of the crystal form of aripiprazole type I microcrystal, and it is provided with excellent crystal form stability and chemical stability.

3. In one of the preferred embodiments of the present invention, an aripiprazole type I microcrystal with average particle size of less than 20 micron is provided, and due to its smaller particle size, the microcrystal has better solubility and bioavailability relative to the existing aripiprazole type I microcrystal.

DETAILED DESCRIPTION OF THE PREFERRED EMBODIMENT

Figure 1:
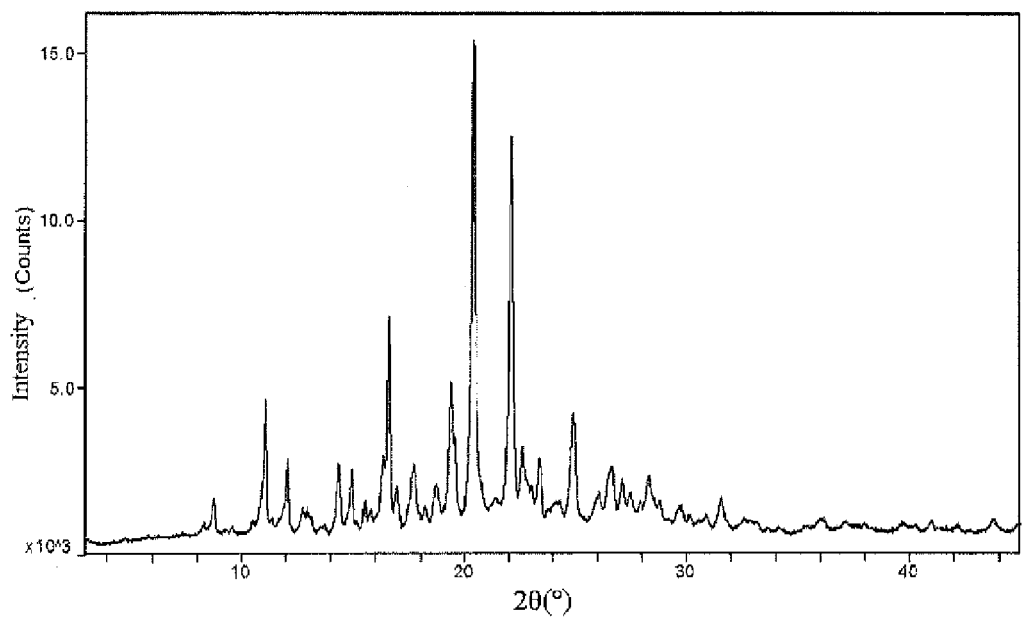
FIG. 1 is the X-ray diffraction spectrum of the aripiprazole type I microcrystal obtained in the Contrastive Example 1.

The following examples further illustrate the present invention, but the present invention is not limited thereto. In the following embodiments, the experimental methods without specific conditions can be carried out by conventional conditions or according to the descriptive literature.

In the following embodiments, drug specification is count as the dosage of aripiprazole, for example, 5 mg/tablet refers to that one tablet contains 5 mg of aripiprazole. Dosage unit is gram, and percentage is mass percentage.

Comparison Example 1

Preparation of Aripiprazole Type I Microcrystal (Preparation according to Chinese Patent Application Publication No.: CN101172966A)

Add 20 g of coarse-grain aripiprazole and 240 ml ethanol into a three-necked reaction flask with reflux condenser, stir and heat them to reflux until complete dissolution of the aripiprazole, then stop heating, adjust linear speed of stirrer to 500 m/min, add 77 ml 1° C. low-temperature water at the same time, put the ice water mixture outside the reaction flask to cool down quickly for 30 min, filter, wash, and dry the obtained crystal in a 80° C. desiccator for 10 hours with decompression to obtain of powdery aripiprazole type I crystal.

Comparison Example 2

Prescription and Wet Preparation Method of Aripiprazole Tablets (10 mg/Tablet) (Dosage Unit: Gram)

| | |
|---|---|
| Drug | Aripiprazole 10 g (microcrystal obtained in Example 2) |
| Adjuvants | Lactose 152 g, Microcrystalline Cellulose 60 g, Povidone K-30 5 g, Sodium Carboxymethyl Starch 12 g, Magnesium Stearate 1.2 g, 75% Aqueous Ethanol Solution 37 g |

-continued

| Preparation Technology | Mix and dilute aripiprazole with the equivalent microcrystalline cellulose, and then add the left microcrystalline cellulose gradually; homogeneously mix them with lactose and 50% amount of carboxymethyl starch sodium; povidone K30 dissolved in 75% aqueous ethanol solution and the above mixture is carried out stirring granulation, finish granule after drying, add magnesium stearate and the left carboxymethyl starch sodium, homogeneously mix and press. |

Comparison Example 3

Prescription and Wet Preparation Method of Aripiprazole Tablets (5 mg/Tablet) (Dosage Unit: Gram)

| Drug | Aripiprazole 5 g (microcrystal obtained in Example 2) |
| Adjuvant | Lactose 65 g, Microcrystalline Cellulose 40 g, Povidone K-30 2 g, Sodium Carboxymethyl Starch 5 g, Starch 30 g, Colloidal Silica 0.2 g, Magnesium Stearate 0.8 g, 50% Aqueous Ethanol Solution 23 g |
| Preparation Technology | Homogeneously mix aripiprazole, microcrystalline cellulose, 50% amount of carboxymethyl starch sodium and starch, add povidone K30 dissolved in 50% aqueous ethanol solution, stir and make into soft material, extrude granulation, finish granule after drying, add colloidal silica and magnesium stearate, homogeneously mix and press into tablets. |

Comparison Example 4

Prescription and Wet Preparation Method of Aripiprazole Capsules (5 mg/Capsule) (Dosage Unit: Gram)

Make the granules before pressing in Comparison Example 3 pass through 30 mesh sieve and homogeneously mix, and add them into capsules.

Example 1

Preparation of Aripiprazole Type I Microcrystal

At room temperature, dissolve the 10 g aripiprazole microcrystals (D[4,3]32.85 mircon) into aqueous ethanol solution containing hydrochloric acid (prepared from 2.3 g 36% hydrochloric acid and 28.5 g anhydrous alcohol, the molar ratio of hydrochloric acid to aripiprazole is 1.02, the mass of aqueous ethanol solution is 3 times that of aripiprazole, the concentration of the aqueous ethanol solution is 95 wt %) to obtain 40.8 g medicament-having acid solution, quickly pour into 9.2 g 10% aqueous sodium hydroxide (the molar ratio of sodium hydroxide to hydrochloric acid is 1.01) while stirring (with stirring linear speed of 160 m/min), stir (with stirring linear speed of 150 m/min) for 5 minutes and then add 100 g water (2.45 times the mass of the medicament-having acid solution) and stir again for 2 minutes, filter the precipitated crystal, wash twice with 20 g water each time and filter each time, dry the crystal at 70° C. for 5 hours with decompression, then obtain 9.6 g aripiprazole microcrystal, the yield is 96%.

Example 2

Preparation of Aripiprazole Type I Microcrystal

At room temperature, dissolve the 10 g crude aripiprazole microcrystal into aqueous ethanol solution containing hydrochloric acid (prepared from 2.5 g 36% hydrochloric acid and 28.5 g anhydrous alcohol, the molar ratio of hydrochloric acid to aripiprazole is 1.11, the mass of aqueous ethanol solution is 3 times that of aripiprazole, the concentration of the aqueous ethanol solution is 95 wt %) to obtain 41 g medicament-having acid solution, add 9.9 g 10% aqueous sodium hydroxide (the molar ratio of sodium hydroxide to hydrochloric acid is 1.00) by dropwise in 1 minute while stirring (with stirring linear speed of 160 m/min), stir (with stirring linear speed of 150 m/min) for 5 minutes and then add 150 g water (3.66 times the mass of the medicament-having acid solution) and stir again for 5 minutes, filter the precipitated crystal, wash twice with 20 g water each time and filter each time, dry the crystal at 60° C. for 4 hours with decompression, then obtain 9.5 g aripiprazole microcrystal, the yield is 95%.

Example 3

Preparation of Aripiprazole Type I Microcrystal

At room temperature, dissolve the 10 g crude aripiprazole microcrystal into aqueous ethanol solution containing hydrochloric acid (prepared from 2.3 g 36% hydrochloric acid and 28.5 g anhydrous alcohol, the molar ratio of hydrochloric acid to aripiprazole is 1.02, the mass of aqueous ethanol solution is 3 times that of aripiprazole, the concentration of the aqueous ethanol solution is 95 wt %) to obtain 40.8 g medicament-having acid solution, slowly add 8 g 10% aqueous sodium hydroxide (the molar ratio of sodium hydroxide to hydrochloric acid is 088) by dropwise (in 1 min) while stirring (with stirring linear speed of 160 m/min), and then slowly add 2.9 g 10% aqueous sodium carbonate (the molar ratio of sodium carbonate to hydrochloric acid is 0.12) by dropwise (in 0.5 min), stir for 2 minutes and then add 100 g water (2.45 times the mass of the medicament-having acid solution) and stir (with stirring linear speed of 150 m/min) again for 5 minutes, filter the precipitated crystal, wash twice with 20 g water each time and filter each time, dry the crystal at 60° C. for 6 hours with decompression, then obtain 9.6 g aripiprazole microcrystal, the yield is 96%.

Example 4

Preparation of Aripiprazole Type I Microcrystal

At room temperature, dissolve the 10 g crude aripiprazole microcrystal into aqueous ethanol solution containing hydrochloric acid (prepared from 2.3 g 36% hydrochloric acid and 30 g anhydrous alcohol, the molar ratio of hydrochloric acid to aripiprazole is 1.02, the mass of aqueous ethanol solution is 3.23 times that of aripiprazole, the concentration of the aqueous ethanol solution is 95 wt %) to obtain 42.3 g medicament-having acid solution, add 30 g lactose while stirring, slowly add 9.1 g 10% aqueous sodium hydroxide (the molar ratio of sodium hydroxide to hydrochloric acid is 1.0) by dropwise (in 1 min) while stirring (with stirring linear speed of 160 m/min), stir (with stirring linear speed of 150 m/min) for 10 minutes and then add 100 g water (236 times the mass of the medicament-having acid solution) and stir again for 5 minutes, filter the precipitated crystal, wash 3 times with 20 g water each time and filter each time, dry the crystal at 70° C. for 5 hours with decompression, then obtain 9.5 g aripiprazole microcrystals, the yield is 95%.

Example 5

Preparation of Aripiprazole Type I Microcrystal

At room temperature, dissolve the 10 g crude aripiprazole microcrystal into aqueous ethanol solution with hydrochloric acid (prepared from 2.3 g 36% hydrochloric acid and 30 g anhydrous alcohol, the molar ratio of hydrochloric acid to aripiprazole is 1.02, the mass of aqueous ethanol solution is 3.23 times that of aripiprazole, the concentration of the aqueous ethanol solution is 95 wt %) to obtain 42.3 g medicament-having acid solution, add 30 g lactose while stirring, slowly add 9.1 g 10% aqueous sodium hydroxide (the molar ratio of sodium hydroxide to hydrochloric acid is 1.0) by dropwise (in 1 min) while stirring (with stirring linear speed of 160 m/min), stir (with stirring linear speed of 150 m/min) for 10 minutes and then add 100 g water (2.36 times the mass of the medicament-having acid solution) and stir again for 5 minutes, carry out the high-speed dispersion in the homogenizer for 10 min, then filter the precipitated crystal, wash 3 times with 20 g water each time and filter each time, dry the crystal at 70° C. for 5 hours with decompression, then obtain 9.5 g aripiprazole microcrystal, the yield is 95%.

Example 6

Prescription and Dry Preparation Method of Aripiprazole Capsules (10 mg/Capsule) (Dosage Unit: Gram)

| | |
|---|---|
| Drug | Aripiprazole 10 g(microcrystal obtained in Example 2) |
| Adjuvants | Anhydrous Lactose 60 g, Microcrystalline Cellulose 40 g, Povidone K-30 2 g, Sodium Carboxymethyl Starch 5 g, Starch 30, Colloidal Silica 0.2 g, Magnesium Stearate 0.8 g |
| Preparation Technology | Homogeneously mix aripiprazole, povidone and 50% amount of microcrystalline cellulose, make them pass through 60 mesh sieve and mix them with other adjuvants homogeneously, add them into hard capsules. |

Example 7

Prescription and Dry Preparation Method of Aripiprazole Capsules (10 mg/Capsule) (Dosage Unit: Gram)

| | |
|---|---|
| Drug | Aripiprazole 10 g(microcrystal obtained in Example 2) |
| Adjuvants | Anhydrous Lactose 60 g, Microcrystalline Cellulose 40 g, Povidone K-30 2 g, Sodium Carboxymethyl Starch 5 g, Starch 30 g, Colloidal Silica 0.2 g, Sodium Stearyl Fumarate 0.8 g |
| Preparation Technology | Homogeneously mix aripiprazole, povidone and 50% amount of microcrystalline cellulose, make them pass through 60 mesh sieve and mix them with other adjuvants homogeneously, add them into hard capsules. |

Example 8

Prescription and Dry Preparation Method of Aripiprazole Capsules (30 mg/Capsule) (Dosage Unit: Gram)

| | |
|---|---|
| Drug | Aripiprazole 30 g(microcrystal obtained in Example 24) |
| Adjuvants | Mannitol 60 g, Microcrystalline Cellulose 60 g, Cross-Linked Polyvinyl Pyrrolidone 10 g, Talc 5 g, Magnesium Stearate 1 g |

| | |
|---|---|
| Preparation Technology | Homogeneously mix aripiprazole and 50% amount of microcrystalline cellulose, make them pass through 60 mesh sieve and mix them with other adjuvants homogeneously, add them into hard capsules. |

Example 9

Prescription and Dry Preparation Method of Aripiprazole Capsules (10 mg/capsule) (Dosage Unit: Gram)

| | |
|---|---|
| Drug | Aripiprazole 5 g (microcrystal obtained in Example 2) |
| Adjuvants | Lactose 65 g, Microcrystalline Cellulose 40 g, Povidone K-30 2 g, Sodium Carboxymethyl Starch 5 g, Starch 30 g, Colloidal Silicon Dioxide 0.2 g, Magnesium Stearate 0.8 g |
| Preparation Technology | Homogeneously mix aripiprazole, povidone and 50% amount of microcrystalline cellulose, make them pass through 60 mesh sieve and mix them with other adjuvants homogeneously, add them into hard capsules. |

Example 10

Prescription and Direct Compression Preparation Method of Aripiprazole Tablets (10 mg/Tablet) (Dosage Unit: Gram)

| | |
|---|---|
| Drug | Aripiprazole 10 g (microcrystal obtained in Contrastive Example 1) |
| Adjuvants | Anhydrous Direct Compression Lactose (DT) 152 g, Microcrystalline Cellulose (pH ~102 NF) 60 g, Povidone K-30 5 g, Sodium Carboxymethyl Starch 12 g, Magnesium Stearate 1.2 g |
| Preparation Technology | Mix and dilute aripiprazole with the equivalent microcrystalline cellulose, and add the left microcrystalline cellulose gradually, mix them with anhydrous direct compression lactose, povidone K-30, sodium carboxymethyl starch, and magnesium stearate, make them pass through 40 mesh sieve, homogeneously mix and press.. |

Example 11

Prescription and Direct Compression Preparation Method of Aripiprazole Tablets (10 mg/Tablet) (Dosage Unit: Gram)

| | |
|---|---|
| Drug | Aripiprazole 10 g (microcrystal obtained in Example 2) |
| Adjuvants | Anhydrous Direct Compression Lactose (DT) 65 g, Microcrystalline Cellulose (pH ~102 NF) 40 g, Cross-Linked Polyvinyl Pyrrolidone 5 g, Colloidal Silica 0.2 g, Magnesium Stearate 0.8 g |
| Preparation Technology | Mix and dilute aripiprazole with the equivalent microcrystalline cellulose, and add the left microcrystalline cellulose gradually, mix them with anhydrous lactose, cross-linked polyvinyl pyrrolidone, colloidal silica and magnesium stearate, make them pass through 40 mesh sieve, homogeneously mix and press.. |

Example 12

Prescription and Direct Compression Preparation Method of Aripiprazole Tablets (5 mg/Tablet) (Dosage Unit: Gram)

| | |
|---|---|
| Drug | Aripiprazole 5 g (microcrystal obtained in Contrastive Example 1) |
| Adjuvants | Composite Lactose (Ludipress LCE) 60 g, Microcrystalline Cellulose (pH ~102 NF) 10 g, Cross-Linked Sodium Carboxymethyl Cellulose 3 g, Colloidal Silica 0.2 g, Magnesium Stearate 0.6 g |

| | -continued |
|---|---|
| Preparation Technology | Mix and dilute aripiprazole with the equivalent microcrystalline cellulose, and add composite lactose, the left microcrystalline cellulose, cross-linked sodium carboxymethyl cellulose, colloidal silica and magnesium stearate, make them pass through 30 mesh sieve, homogeneously mix and press... |

Example 13

Prescription and Direct Compression Preparation Method of Aripiprazole Tablets (5 mg/Tablet) (Dosage Unit: Gram)

10

| | |
|---|---|
| Drug | Aripiprazole 5 g (microcrystal obtained in Example 24) |
| Adjuvants | Composite Lactose (Ludipress LCE) 60 g, Microcrystalline Cellulose (pH ~102 NF) 10 g, Sodium Bisulfite 0.1 g, Cross-Linked Sodium Carboxymethyl Cellulose 3 g, Colloidal Silica 0.2 g, Magnesium Stearate 0.6 g |
| Preparation Technology | Dissolve the sodium bisulfite into water with 6 times its own mass. Homogeneously mix them with the 50% amount of microcrystalline cellulose and make them pass through 24 mesh sieve twice, dry at 70° C., and then make them pass through 80 mesh sieve, to obtain the sodium bisulfite mother powder. Mix and dilute aripiprazole with the equivalent microcrystalline cellulose, and then add composite lactose, cross-linked sodium carboxymethyl cellulose, sodium bisulfite mother powder, colloidal silica and magnesium stearate, make them pass through 30 mesh sieve, homogeneously mix and press. |

Example 14

Prescription and Hot Melting Granulation Preparation Method of Aripiprazole Tablets (5 mg/Tablet) (Dosage Unit: Gram)

30

| | |
|---|---|
| Drug | Aripiprazole 5 g (microcrystal obtained in Example 2) |
| Adjuvants | Lactose 40 g, Microcrystalline Cellulose 35 g, Sodium Bisulfite 0.15 g, Starch 10 g, Powdery Polyethylene Glycol 6000 12 g, Sodium Carboxymethyl Starch 3 g, Colloidal Silica 0.2 g, Magnesium Stearate 0.6 g |
| Preparation Technology | Dissolve the sodium bisulfite into water with 10 times its own mass, add starch and mix them homogeneously, make them pass through 24 mesh sieve twice, dry at 70° C., and then make them pass through 80 mesh sieve, homogeneously mix them with lactose, aripiprazole, microcrystalline cellulose, and powdery polyethylene glycol 6000. Put them into the high speed agitator with jacket temperature at 70~85° C., turn on the blender of the granulator, discharge after the material temperature up to 61° C., cool down, finish granule with 20 mesh sieve, add sodium carboxymethyl starch, colloidal silica and magnesium stearate, homogeneously mix and press. |

Example 15

Prescription and Hot Melting Granulation Preparation Method of Aripiprazole Tablets (10 mg/Tablet) (Dosage Unit: Gram)

50

| | |
|---|---|
| Drug | Aripiprazole 10 g (microcrystal obtained in Contrastive Example 1) |
| Adjuvants | Lactose 30 g, Microcrystalline Cellulose 45 g, L-Cysteine 0.15 g, Starch 10 g, Powdery Polyethylene Glycol 6000 21 g, Cross-Linked Polyvinyl Pyrrolidone 3.5 g, Talc 2.5 g, Magnesium Stearate 0.6 g |
| Preparation Technology | Dissolve the L-cysteine into water with 10 times its own mass, add starch and mix them homogeneously, make them pass through 24 mesh sieve twice, dry at 70° C., and then make them pass through 80 mesh sieve, homogeneously mix them with lactose, aripiprazole, microcrystalline cellulose, and powdery polyethylene glycol 6000. Put them into the high speed agitator with jacket temperature at 70~85° C., turn on the blender of the granulator, discharge after the |

-continued

|   |   |
|---|---|
|   | material temperature up to 61° C., cool down, finish granule with 20 mesh sieve, add cross-linked polyvinyl pyrrolidone, talc and magnesium stearate, homogeneously mix and press |

Example 16

Prescription and Hot Melting Granulation Preparation Method of Aripiprazole Tablets (5 mg/Tablet) (Dosage Unit: Gram)

| | |
|---|---|
| Drug | Aripiprazole 5 g (microcrystal obtained in Example 2) |
| Adjuvants | Lactose 50 g, Microcrystalline Cellulose 50 g, Povidone K-30 2 g, Sodium sulfite 0.1 g, Sodium Carboxymethyl Starch 6 g, Powdery Polyethylene Glycol 6000 12 g, Colloidal Silica 0.2 g, Sodium Stearyl Fumarate 0.6 |
| Preparation Technology | Dissolve the sodium sulfite into water with 10 times its own mass, add 20% amount of microcrystalline cellulose, mix them homogeneously, make them pass through 24 mesh sieve twice, dry at 70° C., and then make them pass through 80 mesh sieve, homogeneously mix them with lactose, aripiprazole, the left microcrystalline cellulose, povidone, 50% amount of sodium carboxymethyl starch and powdery polyethylene glycol 6000. Put them into the high speed agitator with jacket temperature at 70~85° C., turn on the blender of the granulator, discharge after the material temperature up to 62° C., cool down, finish granule with 20 mesh sieve, add colloidal silica 50% amount of sodium carboxymethyl starch and sodium stearyl fumarate, homogeneously mix and press. |

Example 17

Prescription and Hot Melting Granulation Preparation Method of Aripiprazole Capsules (5 mg/Capsule) (Dosage Unit: Gram)

Make the granules before pressing in Example 16 (including colloidal silica and sodium stearyl fumarate) pass through 30 mesh sieve, mix homogeneously and add them into capsules.

Example 18

Prescription and Dry Preparation Method of Aripiprazole Orally Disintegrating Tablets (10 mg/Tablet) (Dosage Unit: Gram)

| | |
|---|---|
| Drug | Aripiprazole 10 g (microcrystal obtained in Contrastive Example 1) |
| Adjuvants | Direct Compression Mannitol (PEARLITOL 200SD) 150 g, Microcrystalline Cellulose (pH ~102 NF) 10 g, Cross-Linked Polyvinyl Pyrrolidone 4 g, Magnesium Stearate 2.6 g |
| Preparation Technology | Mix and dilute aripiprazole with the microcrystalline cellulose, and then mix them with direct compression mannitol, cross-linked polyvinyl pyrrolidone and magnesium stearate, make them pass through 30 mesh sieve, homogeneously mix and press. |

Example 19

Prescription and Dry Preparation Method of Aripiprazole Capsules (10 mg/Capsule) (Dosage Unit: Gram)

| | |
|---|---|
| Drug | Aripiprazole 10 g ((microcrystal obtained in Example 24) |
| Adjuvants | Anhydrous Lactose 180 g, Starch 80 g, Povidone K-30 4 g, Sodium Carboxymethyl Starch 4 g, Magnesium Stearate 2 g |
| Preparation Technology | Mix aripiprazole with the povidone and 20% amount of starch homogeneously, make them pass through 60 mesh sieve, mix them with other adjuvants homogeneously, add them into hard capsules. |

Example 20

Prescription and Dry Preparation Method of Aripiprazole Capsules (20 mg/Capsule) (Dosage Unit: Gram)

| | |
|---|---|
| Drug | Aripiprazole 20 g (microcrystal obtained in Example 2) |
| Adjuvants | Anhydrous Lactose 40 g, Pregelatinized Starch 40 g, Hydroxypropyl Cellulose 5 g, Starch 20 g, Colloidal Silica 0.2 g, Magnesium Stearate 0.8 g |
| Preparation Technology | Mix aripiprazole with the starch homogeneously, make them pass through 60 mesh sieve, mix them with other adjuvants homogeneously, add them into hard capsules. |

Example 21

Prescription and Dry Preparation Method of Aripiprazole Capsules (10 mg/Capsule) (Dosage Unit: Gram)

| | |
|---|---|
| Drug | Aripiprazole 10 g (microcrystal obtained in Contrastive Example 1) |
| Adjuvants | Lactose 40 g, Microcrystalline Cellulose 40 g, Starch 20 g, Sodium Bisulfite 0.1 g, Cross-Linked Polyvinyl Pyrrolidone 8 g, Colloidal Silica 0.2 g, Magnesium Stearate 0.8 g |
| Preparation Technology | Dissolve the sodium bisulfite into water with 10 times its own mass, add 50% amount of starch, mix them homogeneously, make them pass through 24 mesh sieve twice, dry at 70° C., and then make them pass through 80 mesh sieve, homogeneously mix them with aripiprazole and starch homogeneously, make them pass through 60 mesh sieve, mix them with other adjuvants homogeneously, add them into hard capsules. |

Example 22

Preparation of Aripiprazole Type I Microcrystal

At room temperature, prepare the 20 g anhydrous alcohol, 10 g glycerol, 2.3 g 36% hydrochloric acid and 10 g aripiprazole into 42.3 g medicament-having acid solution (the molar ratio of hydrochloric acid to aripiprazole is 1.02, the mass of the alcoholic solution is 3 times that of aripiprazole, the concentration of the alcoholic solution is 95 wt %), add 9.2 g 10% aqueous sodium hydroxide (the molar ratio of sodium hydroxide to hydrochloric acid is 1.0) by dropwise all at once while stirring (with stirring linear speed of 160 m/min), stir for 5 minutes and then add 100 g water (2.4 times the mass of the medicament-having acid solution) and stir again for 2 minutes, then filtrate the precipitated crystal, wash twice with 20 g water each time and filter each time, dry the crystal at 70° C. for 6 hours with decompression, then obtain 9.5 g aripiprazole microcrystal.

Example 23

Preparation of Aripiprazole Type-I Microcrystals

At room temperature, prepare the 20 g anhydrous alcohol, 10 g glycerol, 2.3 g 36% hydrochloric acid and 10 g aripiprazole into 42.3 g medicament-having acid solution (the molar ratio of hydrochloric acid to aripiprazole is 1.02, the mass of the alcoholic solution is 3 times that of aripiprazole, the concentration of the alcoholic solution is 95 wt %), add 9.2 g 10% aqueous sodium hydroxide (the molar ratio of sodium hydroxide to hydrochloric acid is 1.01) by dropwise all at once while stirring (with stirring linear speed of 160 m/min), stir for 5 minutes and then add 100 g water (2.4 times the mass of the medicament-having acid solution) and stir again for 2 minutes, then filtrate the precipitated crystal, wash with 15 g water and filtrate, then wash with 15 g 60% aqueous ethanol solution and filtrate, dry the crystal at 70° C. for 5 hours with decompression, then obtain 9.6 g aripiprazole microcrystal.

Example 24

Preparation of Aripiprazole Type I Microcrystal

At room temperature, dissolve 10 g aripiprazole and 10 g povidone K-30 into aqueous ethanol solution containing hydrochloric acid (prepared from 2.4 g 36% hydrochloric acid and 30 g anhydrous alcohol, the molar ratio of hydrochloric acid to aripiprazole is 1.08, the mass of aqueous ethanol solution is 3.24 times that of aripiprazole) to obtain 52.4 g medicament-having acid solution, add 50 g mannitol while stirring, slowly add (for 1 min) 9.7 g 10% aqueous sodium hydroxide (the molar ratio of sodium hydroxide to hydrochloric acid is 1.02) by dropwise while stirring (with stirring linear speed of 300 m/min), stir for 5 minutes and then add 150 g water (2.86 times the mass of the medicament-having acid solution) and stir again for 5 minutes, filtrate the precipitated crystal, wash twice with 30 g water each time and filtrate each time, then wash with 20 g 50% aqueous ethanol solution and filtrate, dry the crystals at 70° C. for 5 hours with decompression, then obtain 9.2 g aripiprazole microcrystal, the yield is 92%.

Effect Example 1

Measure the particle size of aripiprazole in the sample by the following methods, and compare the particle size of aripiprazole in different prescriptions and under different operating conditions.

Test Instrument: BT~9300S laser particle size distribution analyzer (Dandong Baxter technology Co., Ltd); BT~800 automatic loop sampling system.

Test conditions: the medium of the loop sampling system is water, with the volume of about 570 ml, and the centrifugal pump speed is 1600 rpm.

Test Method: add appropriate amount of the samples into the loop sampling system, and make the absorbance of the system up to 15%±10, turn on the ultrasonic dispersion for 3 min, continuous sample for 6 times, and gain the average particle size.

1. Dissolve 10 g aripiprazole into aqueous ethanol solution containing hydrochloric acid (the molar ratio of hydrochloric acid to aripiprazole is 1.1, the concentration of the aqueous ethanol solution is 95%, the mass of the aqueous ethanol solution is 30 g), quickly add the 10% aqueous sodium hydroxide (the molar ratio of sodium hydroxide to hydrochloric acid is 1.01) all at once while stirring. Stir for 5 min then add 100 g water, stir again for 5 min, filter the precipitated crystal, wash twice with 20 g water each time and filter each time, dry the crystal at 80° C. for 4 hours, then obtain the aripiprazole microcrystal. The test results are shown in Table 1.

TABLE 1 the table of the comparison on the particle sizes

| Serial Number | stirring linear speed (m/min) | particle size (micron) | | | |
|---|---|---|---|---|---|
| | | D[4,3] | $D_{10}$ | $D_{50}$ | $D_{90}$ |
| 1~1 | 40 | 30.80 | 4.62 | 26.40 | 62.70 |
| 1~2 | 160 | 14.17 | 1.85 | 10.91 | 29.82 |
| 1~3 | 245 | 13.80 | 1.64 | 9.97 | 26.01 |

Note:
D[4,3] is the volume average diameter; $D_{10}$, $D_{50}$ and $D_{90}$ are correspondingly particle sizes when the percentages of cumulative particle size distribution are up to 10%, 50% and 90% respectively.

2. Dissolve 10 g aripiprazole into aqueous ethanol solution with hydrochloric acid (the molar ratio of hydrochloric acid to aripiprazole is 1.02), quickly add the 10% aqueous sodium hydroxide (the molar ratio of sodium hydroxide to hydrochloric acid is 1.0) all at once while stirring (with stirring linear speed of 160 m/min). Stir for 5 min then add 100 g water, stir again for 5 min, filter the precipitated crystal, wash twice with 20 g water each time and filter each time, dry the crystals at 80° C. for 4 hours, then obtain the aripiprazole microcrystal. The test results are shown in Table 2.

TABLE 2 the table of the comparison on the particle sizes

| Serial Number | the concentration of the aqueous ethanol solution (%) W/W | Aripiprazole:aqueous ethanol solution in the medicament-having acid solution | particle size (micron) | | | |
|---|---|---|---|---|---|---|
| | | | D[4,3] | $D_{10}$ | $D_{50}$ | $D_{90}$ |
| 2-1 | 50 | 1:3 | 31.87 | 5.59 | 27.29 | 63.62 |
| 2-2 | 75 | 1:3 | 39.99 | 6.41 | 31.11 | 88.10 |
| 2-3 | 85 | 1:3 | 28.42 | 3.77 | 23.47 | 60.51 |
| 2-4 | 95 | 1:3 | 14.17 | 1.85 | 10.91 | 29.82 |
| 2-5 | 95 | 1:2 | 20.75 | 2.41 | 15.11 | 48.59 |
| 2-6 | 95 | 1:5 | 36.12 | 6.10 | 28.09 | 77.61 |

3. Dissolve 10 g aripiprazole into aqueous ethanol solution with hydrochloric acid (2.3 g 36% hydrochloric acid, 28.5 g anhydrous ethanol. The concentration of the aqueous ethanol solution is 95%), add the 10% aqueous sodium hydroxide (the molar ratio of sodium hydroxide to hydrochloric acid is 1.0) while stirring (with stirring linear speed of 160 m/min). Stir for 5 min then add 100 g water, stir again for 5 min, filter the precipitated crystal, wash twice with 20 g water each time and filter each time, dry the crystal at 80° C. for 4 hours, then obtain the aripiprazole microcrystal. The test results are shown in Table 3.

TABLE 3 the table of the comparison on the particle sizes

| Serial Number | Adding methods of the 10% aqueous sodium hydroxide | particle size (micron) | | | |
|---|---|---|---|---|---|
| | | D[4,3] | $D_{10}$ | $D_{50}$ | $D_{90}$ |
| 3-1 | Quickly adding all at once (within 0.05 min) | 45.41 | 6.22 | 25.71 | 140.32 |
| 3-2 | Moderately adding all at once (drop for 0.2 min) | 24.25 | 3.42 | 21.39 | 48.63 |
| 3-3 | Slowly adding all at once (drop for 0.5 min) | 15.67 | 1.07 | 13.35 | 33.07 |
| 3-4 | Quickly adding by two separate times with the interval of 0.5 min | 24.57 | 3.34 | 19.59 | 53.42 |

Effect Example 2

The Testing Results of the Particle Sizes

The table of the testing results of the particle sizes

| Examples | particle size (micron) | | | |
|---|---|---|---|---|
| | D[4,3] | $D_{10}$ | $D_{50}$ | $D_{90}$ |
| Contrastive Example 1 | 32.85 | 9.31 | 29.85 | 60.39 |
| 2 | 14.17 | 1.85 | 10.91 | 29.82 |
| 3 | 15.64 | 1.43 | 11.64 | 34.65 |
| 4 | 10.99 | 1.18 | 8.78 | 24.78 |
| 5 | 6.79 | 0.74 | 4.75 | 16.34 |
| 23 | 13.42 | 1.52 | 9.67 | 32.17 |
| 24 | 4.73 | 1.00 | 3.93 | 8.7 |

Effect Example 3

Comparison Experiments on Solubility

Method of Solubility Experiment: following solubility mensuration (Chinese Pharmacopoeia 2010 Volume 2 appendix X C No. 2), take sample and make 500 ml pH 4.0 acetate buffer solution (0.05 mol/L acetic acid–0.05 mol/L sodium acetate=16.4:3.6) as solvent, rotation rate is 75 rpm, carry out according to the mensuration, take 5 ml solution at the 5th, 10th, 20th, 30th, 45th min respectively, replenish 5 ml dissolution medium to each dissolution cup, filter the samples, take subsequent filtrate as sample solution, and prepare the reference solution. Detection is respectively followed by high performance liquid chromatography (Chinese Pharmacopoeia 2010 Volume 2 appendix □ D), and use octadecylsilane chemically bonded silica as filler; and use methyl alcohol ~0.1% triethylamine solution (90:10) as mobile phase; detection wavelength is at 255 nm, and calculate the solubility of each tablet.

|         | Solubility (%) |         |         |         |
|---------|----------------|---------|---------|---------|
| Example | 10 min         | 20 min  | 30 min  | 45 min  |
| 6       | 82.5           | 94.3    | 99.2    | 99.3    |
| 7       | 80.6           | 92.7    | 96.4    | 98.6    |
| 10      | 78.6           | 90.9    | 95.3    | 98.4    |
| 16      | 65.0           | 88.5    | 95.3    | 97.7    |
| 19      | 85.6           | 99.1    | 99.5    | 99.5    |

Effect Example 4

Comparison Experiments on Stability (1) Add samples into high density polyethylene plastic bottle respectively and package them, put them under the condition of temperature 40° C.±2° C. and relative humidity 75%±5%, after the accelerated test for 3 months, take the samples and carry out the detection of character, content, solubility and related substances.

Detection Method of Content and the Related Substances: take appropriate dosage of samples, shake and dissolve it by mobile phase ultrasonic and make the solution containing appropriate aripiprazole per ml as the tested solution, and prepare reference solution. Detection is respectively followed by high performance liquid chromatography (Chinese Pharmacopoeia 2010 Volume 2 appendix □ D), and use octadecylsilane chemically bonded silica as filler; use methyl alcohol~acetic acid solution (add 1 ml triethylamine into 1000 ml water, and adjust the pH to 4.0 by acetic acid) (60:40) as mobile phase; detection wavelength is at 255 nm. The determination of content is according to the external standard method, the content of the related substance is calculated by main component self-contrast method, and the result data is shown in the following table.

|  | Character | | Content (%) | | Solubility at the 45$^{th}$ min (%) | | Related Substance (%) | |
|---|---|---|---|---|---|---|---|---|
| Example | Prior to acceleration | After acceleration | Prior to acceleration | After acceleration | Prior to acceleration | After acceleration | Prior to acceleration | After acceleration |
| Contrastive 2 | White tablet | White tablet | 99.1 | 98.9 | 98.7 | 97.3 | 0.10 | 0.30 |
| Contrastive 3 | White tablet | White tablet | 99.5 | 99.4 | 99.2 | 99.3 | 0.09 | 0.33 |
| 6 | Content is white | Content is white | 99.5 | 99.4 | 99.3 | 99.1 | 0.02 | 0.05 |
| 7 | Content is white | Content is white | 99.3 | 99.4 | 98.6 | 99.0 | 0.02 | 0.05 |
| 10 | White tablet | White tablet | 99.8 | 99.9 | 98.4 | 99.1 | 0.05 | 0.10 |
| 16 | White tablet | White tablet | 100.1 | 99.7 | 98.7 | 97.9 | 0.08 | 0.17 |
| 19 | Content is white | Content is white | 99.6 | 99.5 | 99.5 | 99.6 | 0.03 | 0.06 |

(2) Add samples into high density polyethylene plastic bottle respectively and package them, put them under the condition of temperature 60° C.±2° C. for 20 days, carry out the detection of character, content and related substances.
The test method is the same as above.

|  | Character | | Content (%) | | Related Substance (%) | |
|---|---|---|---|---|---|---|
| Example | Prior to acceleration | After acceleration | Prior to acceleration | After acceleration | Prior to acceleration | After acceleration |
| Contrastive 2 | White tablet | Off-white tablet | 99.1 | 99.0 | 0.10 | 0.33 |
| Contrastive 3 | White tablet | Off-white tablet | 99.5 | 99.6 | 0.09 | 0.35 |

-continued

| Example | Character Prior to acceleration | Character After acceleration | Content (%) Prior to acceleration | Content (%) After acceleration | Related Substance (%) Prior to acceleration | Related Substance (%) After acceleration |
|---|---|---|---|---|---|---|
| 6 | Content is white | Content is white | 99.5 | 99.1 | 0.02 | 0.06 |
| 7 | Content is white | Content is white | 99.3 | 99.4 | 0.02 | 0.07 |
| 10 | White tablet | Off-white tablet | 99.8 | 99.5 | 0.05 | 0.13 |
| 16 | White tablet | Off-white tablet | 100.1 | 99.7 | 0.08 | 0.20 |
| 19 | Content is white | Content is white | 99.6 | 99.7 | 0.03 | 0.07 |

Effect Example 5

Comparison on X-Ray Diffraction Patterns and Crystal Stability (1) The powder X-ray diffraction patterns of aripiprazole type I microcrystal in Contrastive Example 1 (d-Spacing=Cu/k-alpha1), is shown in FIG. 1.

There are characteristic peaks at 2θ=11.05°, 16.62°, 19.38°, 20.39°, 22.08°, 24.92° and 26.64° in the X-ray diffraction patterns. The characteristic peaks of the powder X-ray diffraction patterns is the same with the reference patterns, and it indicate that the aripiprazole microcrystal obtained in that example is type I microcrystal.

Figure 2:
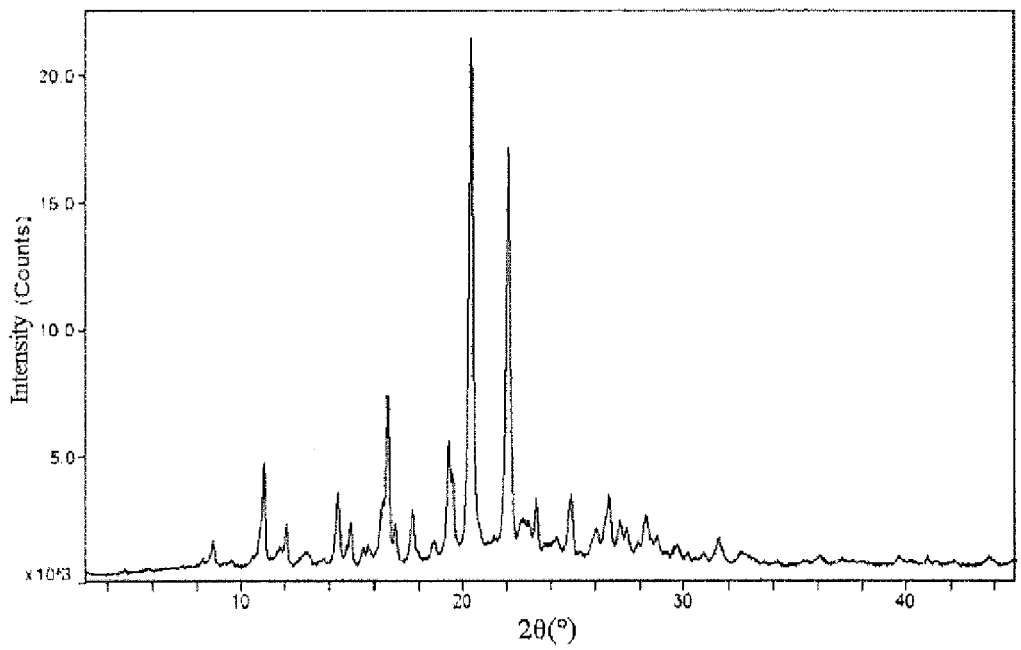
FIG. 2 is the X-ray diffraction spectrum of the aripiprazole type I microcrystal obtained in the Example 2.

(2) The powder X-ray diffraction patterns of aripiprazole type I microcrystal in Contrastive Example 2 (d-Spacing=Cu/k-alpha1), is shown in FIG. 2.

There are characteristic peaks at 2θ=2θ=11.07°, 16.63°, 19.38°, 20.40°, 22.10°, 22.62° and 24.92° in the X-ray diffraction patterns. The characteristic peaks of the powder X-ray diffraction patterns is the same with the reference patterns, and it indicate that the aripiprazole microcrystal obtained in that example is type I microcrystal.

Figure 3:
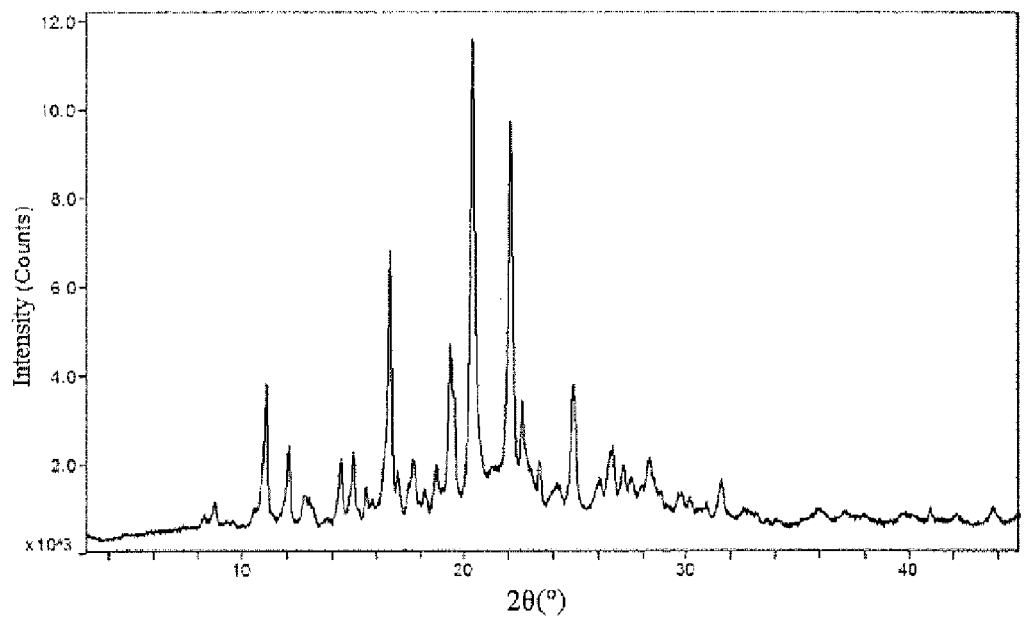
FIG. 3 is the X-ray diffraction spectrum of the aripiprazole type I microcrystal obtained in the Example 24.

(3) The powder X-ray diffraction patterns of aripiprazole type I microcrystal in Contrastive Example 24 (d-Spacing=Cu/k-alpha1), is shown in FIG. 3.

There are characteristic peaks at 2θ=11.07°, 16.64°, 19.40°, 20.41°, 22.10°, 22.64° and 24.92° in the X-ray diffraction patterns. The characteristic peaks of the powder X-ray diffraction patterns is the same with the reference patterns, and it indicate that the aripiprazole microcrystal obtained in that example is type microcrystal.

Figure 4:
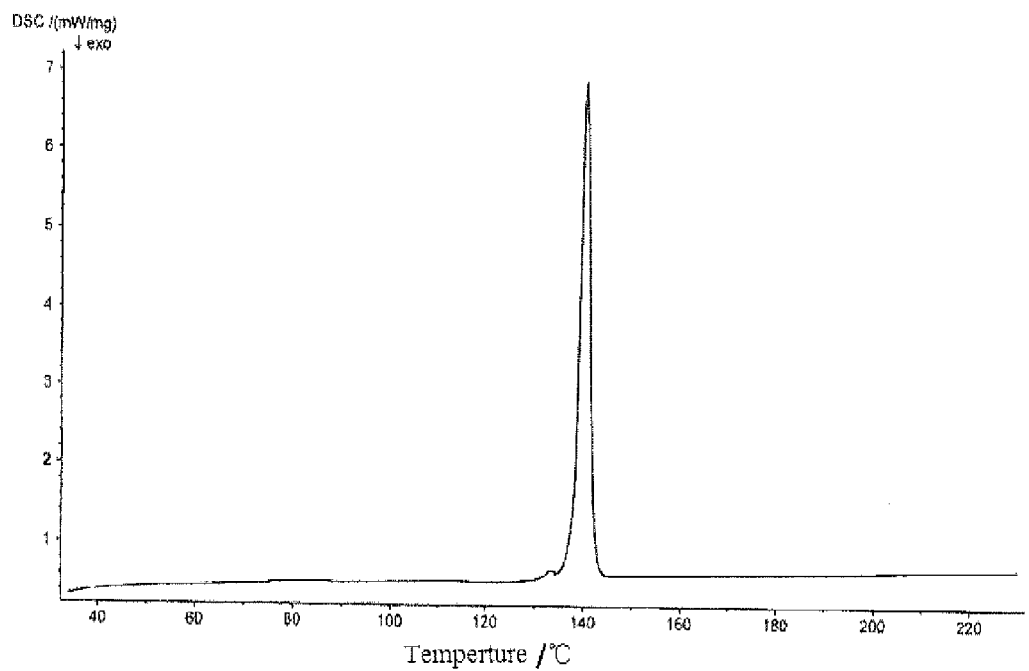
FIG. 4 is the DSC curves of the aripiprazole type I microcrystal obtained in the Example 2.

(4) The differential scanning calorimetry (DSC) curves of aripiprazole type I microcrystal in Example 2 (heating rate is 10.0° C./min), is shown in FIG. 4.

The testing result indicates that, the characteristic endothermic transition is at about 140° C.

Figure 5:
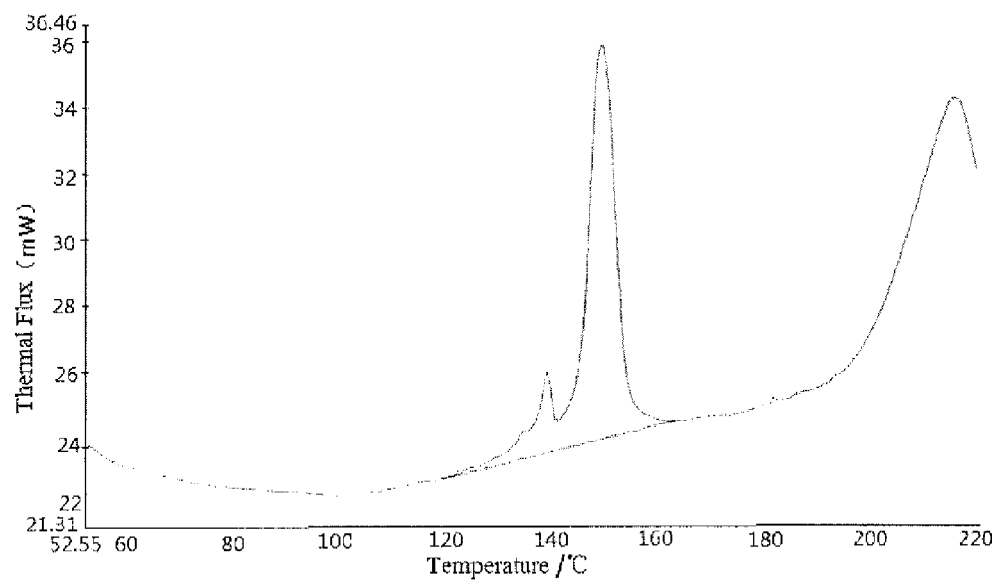
FIG. 5 is the DSC curves of the content material of the aripiprazole capsule of the Contrastive Example 4.

(5) The differential scanning calorimetry (DSC) curves of aripiprazole type I microcrystal in Contrastive Example 4 (heating rate is 10.0° C./min), is shown in FIG. 5.

The testing result indicates that, there is a small transition peak (aripiprazole) at about 140□, and a big transition peak (adjuvants) at about 150° C., with large baseline fluctuation before the aripiprazole transition peak and frontal peak exists.

Figure 6:
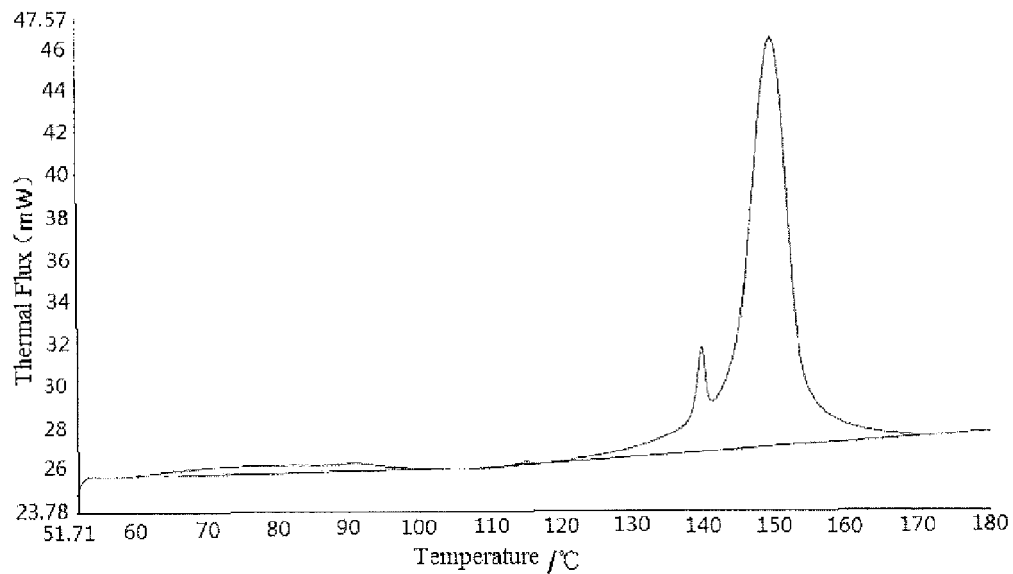
FIG. 6 is the DSC curves of the content material of the aripiprazole capsule of the Example 9.

(6) The differential scanning calorimetry (DSC) curves of aripiprazole type I microcrystal in Example 9 (heating rate is 10.0° C./min), is shown in FIG. 6.

Figure 7:
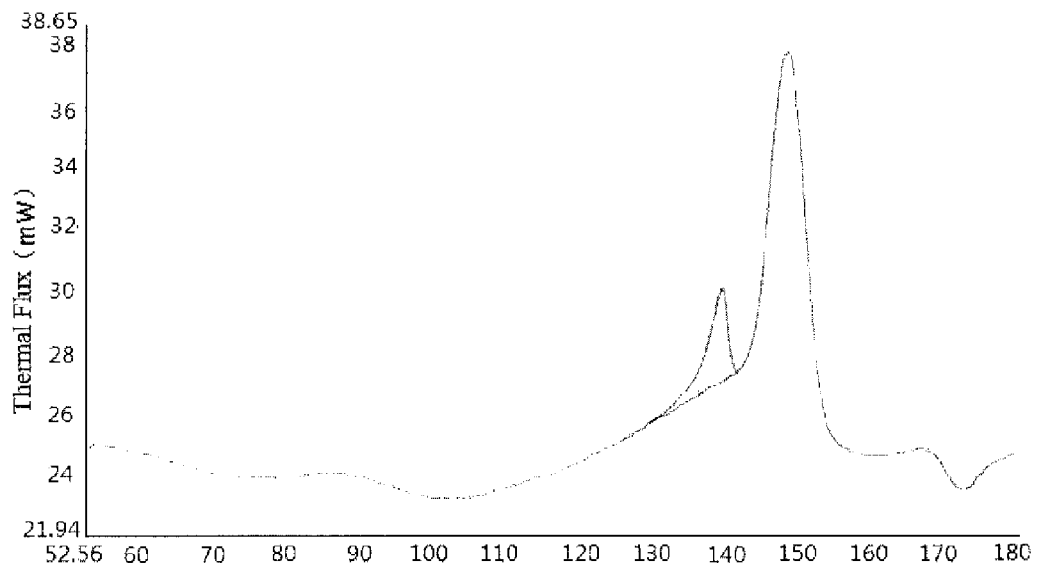
FIG. 7 is the DSC curves of the aripiprazole tablet of the Contrastive Example 3.

The testing result indicates that, there is a small transition peak (aripiprazole) at about 140° C., and a big transition peak (adjuvants) at about 150° C., with stable baseline before the aripiprazole transition peak, (7) The differential scanning calorimetry (DSC) curves of aripiprazole type I microcrystal in Contrastive Example 3 (heating rate is 10.0° C./min), is shown in FIG. 7.

The testing result indicates that, there is a small transition peak (aripiprazole) at about 140° C., and a big transition peak (adjuvants) at about 150° C., with large baseline fluctuation before the aripiprazole transition peak and frontal peak exists.

Analysis: according to the comparison among FIG. 5, FIG. 6 and FIG. 7, the phase transition peaks of these DSC curves are generally the same, but there are large baseline fluctuation before the aripiprazole transition peak in FIG. 5 and FIG. 7 and frontal peak exists (there is larger baseline fluctuation in FIG. 7 than in FIG. 5), so it hints that there are intergrowth crystals phenomenon, and the solvates that affect the stability of the aripiprazole may exist. However, the baseline in FIG. 6 is relatively stable. Dry method with directly adding into capsules is best for crystal stability. In the same wet granulation conditions, directly adding into capsules is more favourable than pressing into tablets.

Figure 8:
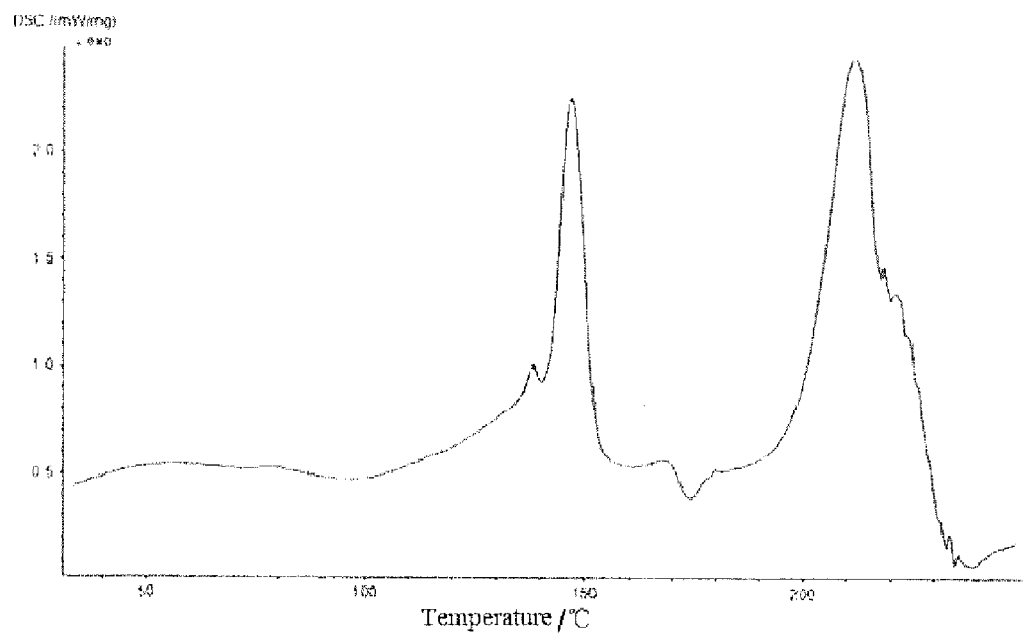
FIG. 8 is the DSC curves of the aripiprazole tablet of the Contrastive Example 2.

(8) The differential scanning calorimetry DSC curves of aripiprazole type microcrystal in Contrastive Example 2 (heating rate is 10.0° C./min), is shown in FIG. 8.

The testing result indicates that, there is a small transition peak (aripiprazole) at about 140° C., and there is big transition peak (adjuvants) at 150° C. and 210° C. separately, with large baseline fluctuation before the aripiprazole transition peak and frontal peak exists.

Figure 9:
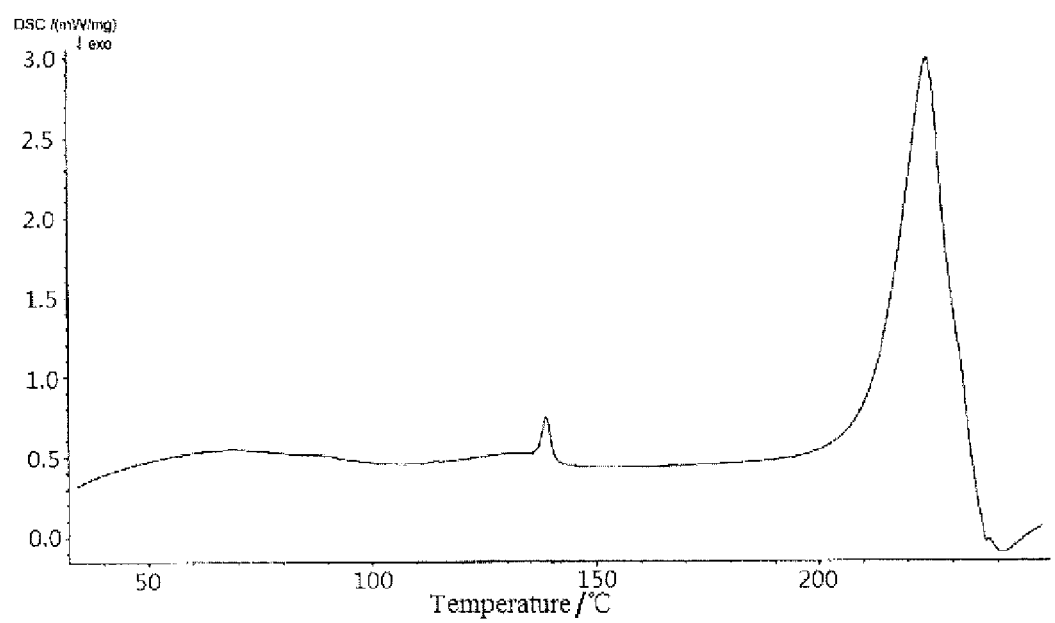
FIG. 9 is the DSC curves of the aripiprazole tablet of the Example 10.

(9) The differential scanning calorimetry DSC curves of aripiprazole type microcrystal in Example 10 (heating rate is 10.0° C./min), is shown in FIG. 9.

The testing result indicates that, there is a small transition peak (aripiprazole) at about 140° C., and a big transition peak (adjuvants) at 220° C., and there is generally no frontal peak before the aripiprazole transition peak.

Analysis:

According to the comparison between FIG. 8 and FIG. 9, the baseline of FIG. 9 is stable, and the phase transition peaks at about 140° C. is sharp, basically without frontal peak; but the frontal peak of FIG. 8 has big area, and the solvates that affect the stability of the aripiprazole may exist. The proportioning in Contrastive Example 2 and Example 10 is the same, and the lactose in Contrastive Example 2 is ordinary lactose, and method of tableting after wet granulation is used; the lactose in Example 10 is anhydrous direct compression lactose, and dry direct tableting is used. For the crystal stability, the dry direct tableting is obviously superior to tableting after wet granulation.

What is claimed is:

1. A method of preparing an aripiprazole type I microcrystal having an average particle size of no more than 50 µm, comprising:
adding aripiprazole to an aqueous ethanol solution containing an acid to dissolve the aripiprazole and obtain a medicament-having acid solution;
adding an alkalizer while stirring at room temperature;
then adding water or 10-60 wt. % aqueous ethanol while stirring at room temperature; and
separating a precipitated aripiprazole type I microcrystal.

2. The method according to claim 1, wherein said aripiprazole is an aripiprazole type I microcrystal having an average particle size greater than that of the separated and precipitated aripiprazole type I microcrystal, an aripiprazole type II microcrystal, or an amorphous aripiprazole.

3. The method according to claim 1, wherein:
said acid is one or more selected from the group consisting of hydrochloric acid, lactic acid, and malic acid; and
an amount of said acid is 1-1.2 times greater than a minimum amount of said acid that is necessary to completely dissolve the aripiprazole.

4. The method according to claim 3, wherein:
when the acid is hydrochloric acid, a molar ratio of hydrochloric acid to aripiprazole is 0.8:1-1.2:1; and
when the acid is lactic acid, a molar ratio of lactic acid to aripiprazole is 1.8:1-2.5:1.

5. The method according to claim 1, wherein:
an amount of said aqueous ethanol in the aqueous ethanol solution is no less than twice a mass of the aripiprazole that is added to the aqueous ethanol solution.

6. The method according to claim 1, further comprising adding one or more additives selected from the group consisting of a surfactant, a solubilizer, and a water-soluble carrier before adding the alkalizer; wherein:
said surfactant and/or solubilizer is one or more selected from the group consisting of povidone, sodium lauryl sulfate, poloxamer, polyoxyethylene castor oil, Tween-80, and polyoxyl 40 stearate;
said water-soluble carrier is one or more selected from the group consisting of lactose, mannitol, sucrose, polyethylene glycol, hydroxypropyl β cyclodextrin, and maltitol;
said polyethylene glycol is polyethylene glycol 400-8000;
said surfactant and/or solubilizer are added while preparing the medicament-having acid solution, or after obtaining said medicament-having acid solution;
when said water-soluble carrier is one or more of polyethylene glycol and hydroxypropyl β cyclodextrin, said water-soluble carrier is added while preparing the medicament-having acid solution or after obtaining said medicament-having acid solution; and
when said water-soluble carrier is one or more of lactose, mannitol, sucrose, and maltitol, said water-soluble carrier is added after obtaining said medicament-having acid solution.

7. The method according to claim 6, wherein:
an amount of said water-soluble carrier is 1-5 times a mass of the aripiprazole that is added to the aqueous ethanol solution, and
an amount of said surfactant and/or solubilizer is 0.01-2.0 times the mass of the aripiprazole that is added to the aqueous ethanol solution.

8. The method according to claim 1, further comprising increasing a temperature to 30-85° C. while preparing the medicament having acid solution.

9. The method according to claim 1, wherein said alkalizer is one or more selected from the group consisting of sodium hydroxide, potassium hydroxide, sodium carbonate, potassium carbonate, and disodium hydrogen phosphate.

10. The method according to claim 9, wherein:
said alkalizer is added as an alkalizer solution comprising a solvent, and
a concentration of the alkalizer in the alkalizer solution is 5-20 wt %.

11. The method according to claim 9, wherein:
the acid is hydrochloric acid, and the alkalizer is one or more selected from the group consisting of sodium hydroxide, sodium carbonate, and a combination thereof; and
a molar ratio of sodium hydroxide, sodium carbonate, or the combination thereof to hydrochloric acid is 0.95:1-12:1.

12. The method according to claim 10, further comprising adding the alkalizer by directly pouring or dropping the alkalizer into the medicament-having acid solution within a time period of 0.5-2 minutes.

13. The method according to claim 1, wherein the solution is stirred for 2-10 minutes after adding the alkalizer and before adding the water or 10-60 wt. % aqueous ethanol while stirring.

14. The method according to claim 1, wherein an amount of said water or 10-60 wt. % aqueous ethanol is no less than twice a mass of said medicament-having acid solution.

15. The method according to claim 1, further comprising stirring the solution for 2-5 minutes after adding the water or 10-60 wt. % aqueous ethanol and then separating said precipitated aripiprazole type I microcrystal.

16. The method according to claim 1, further comprising carrying out a dispersion treatment via a colloid mill or a homogenizer before separating said precipitated aripiprazole type I microcrystal.

17. The method according to claim 1, wherein:
said separating comprises filtrating, washing and filtrating, and drying said precipitated aripiprazole type I microcrystal;
said precipitated aripiprazole type I microcrystal is washed with water or 10-60 wt % aqueous ethanol;
each washing is carried out with an amount of the water or 10-60 wt. % aqueous ethanol that is 1-5 times a mass of said aripiprazole that is added to the aqueous ethanol solution;
the precipitated aripiprazole type I microcrystal is washed and filtrated 1-3 times;
said drying comprises static drying or dynamic drying;
said static drying is carried out at 40-100° C. and a vacuum condition of decompression of 450 mmHg-76 mmHg; and
said dynamic drying is carried out at 50-80° C. in a vacuo double cone drying mixer for 2-6 hours.

18. The method according to claim 1, wherein a linear speed of said stirring is 150-500 m/min.

19. The method according to claim 1, wherein:
the acid is hydrochloric acid;
a concentration of the aqueous ethanol solution is no less than 95 wt %;
said alkalizer is added as an aqueous solution of sodium hydroxide and/or sodium carbonate while stirring;
when the alkalizer is sodium hydroxide, a molar ratio of sodium hydroxide to hydrochloric acid is 0.95:1-1:1;
when the alkalizer is sodium carbonate, a molar ratio of sodium carbonate to hydrochloric acid is 0.9:1-1:1;

when the alkalizer is sodium hydroxide and sodium carbonate, a molar ratio of sodium hydroxide to hydrochloric acid is 0.85:1-0.9:1, and a molar ratio of sodium carbonate to hydrochloric acid is 0.11:1-0.13:1;

after the alkalizer is added, the solution is stirred for 2-10 minutes at a stirring linear speed in a range of 150 to 500 m/min, and then the water is added while continuing to stir the solution at a stirring speed in a range of 150 to 500 m/min;

after the water is added, the solution is then stirred for 2-5 minutes at a stirring linear speed in a range of 150 to 500 m/min, and then the precipitated aripiprazole type I microcrystal is separated by filtrating, washing and filtrating, and then drying the precipitated aripiprazole type I microcrystal; and the aripiprazole type I microcrystal has an average particle size of less than 20 μm.

20. The method according to claim 19, wherein:

a molar ratio of hydrochloric acid to aripiprazole is 1:1-1.1:1;

an amount of said aqueous ethanol solution is 2.5-3.5 times a mass of the aripiprazole that is added to the aqueous ethanol solution;

said aqueous solution of the alkalizer is added by directly pouring or dropping said aqueous solution of the alkalizer into the medicament-having acid solution within a time period of 0.5-2 minutes;

a concentration of said aqueous solution of the alkalizer is 5-15 wt %;

an amount of said water is 2-4 times a mass of said medicament-having acid solution;

the precipitated aripiprazole type I microcrystal is washed twice or three times with water or 30-60 wt % aqueous ethanol; and each washing is carried out with an amount of the water or 30-60 wt. % aqueous ethanol that is 1-5 times the mass of the aripiprazole that is added to the aqueous ethanol solution.

21. The method of according to claim 20, further comprising:

adding one or more selected from the group consisting of a surfactant, a solubilizer, and a water-soluble carrier to the solution before adding the alkalizer, and/or carrying out a dispersion treatment via a homogenizer or a colloid mill for more than 10 minutes before separating the precipitated aripiprazole type I microcrystal, wherein:
said surfactant and/or solubilizer is povidone,
an amount of said surfactant and/or solubilizer is 0.8-1.2 times greater than the mass of the aripiprazole that is added to the aqueous ethanol solution,
said water-soluble carrier is lactose and/or mannitol, and
an amount of said water-soluble carrier is 2.5-3.5 times the mass of the aripiprazole that is added to the aqueous ethanol solution.

22. A method of preparing a solid preparation comprising an aripiprazole type I microcrystal, the method comprising:

(1) preparing the aripiprazole type I microcrystal according to the method of claim 1, and (2) preparing an aripiprazole tablet or capsule via a dry method by mixing the aripiprazole type I microcrystal and adjuvants.

23. The method according to claim 22, wherein said dry method comprises:

homogeneously mixing the aripiprazole type I microcrystal and adjuvants to form a powder;

optionally acquiring granules by hot melt granulation processing of the powder; and then directly adding the powder or granules into a capsule to obtain a capsule preparation, or directly pressing the powder or granules into a tablet to obtain a tablet.

24. The method according to claim 23, wherein:

when the powder is added into the capsule to obtain the capsule preparation:
said adjuvants comprise a filler, a disintegrant, and a lubricant;
said filler is one or more selected from the group consisting of lactose, anhydrous lactose, mannitol, microcrystalline cellulose, starch, xylitol, pregelatinized starch, and maltitol;
said disintegrant is one or more selected from the group consisting of sodium carboxymethyl starch, hydroxypropyl cellulose, cross-linked polyvinyl pyrrolidone, and cross-linked sodium carboxymethylcellulose;
said lubricant is one or more selected from the group consisting of colloidal silica, sodium stearyl fumarate, talc, and magnesium stearate;
a sum of an amount of said filler and a water-soluble carrier is 70-95 mass % based on a total mass of a content of the capsule;
an amount of said disintegrant is 2-8% mass % based on the total mass of the content of the capsule; and
an amount of said lubricants is 0.5-4 mass % based on the total mass of the content of the capsule; or when the powder is pressed into the tablet by a direct compression process to obtain the tablet:
said adjuvants comprise a direct compression adjuvant, a disintegrant, and a lubricant;
said direct compression adjuvant is one or more selected from the group consisting of direct compression lactose, direct compression mannitol, direct compression microcrystalline cellulose, and direct compression complexes;
said disintegrant is one or more selected from the group consisting of sodium carboxymethyl starch, hydroxypropyl cellulose, cross-linked polyvinyl pyrrolidone, and cross-linked sodium carboxymethylcellulose;
said lubricant is one or more selected from the group consisting of colloidal silica, sodium stearyl fumarate, talc, and magnesium stearate;
a sum of an amount of said direct compression adjuvant and said water-soluble carrier is 80-98 mass % based on a total mass of the tablet;
an amount of said disintegrant is 2-5 mass % based on the total mass of the tablet; and
an amount of said lubricant is 0.5-3 mass % based on the total mass of the tablet; or when the granules are added into the capsule to obtain the capsule preparation or the granules are pressed into the tablet by the direct compression process to obtain the tablet:
said adjuvants comprise a filler, a disintegrant, a lubricant, and a pharmaceutically acceptable water-soluble hot-melt material;
said filler is one or more selected from the group consisting of lactose, anhydrous lactose, mannitol, microcrystalline cellulose, starch, xylitol, pregelatinized starch and maltitol;
said disintegrant is one or more selected from the group consisting of sodium carboxymethyl starch, hydroxypropyl cellulose, cross-linked polyvinyl pyrrolidone and cross-linked sodium carboxymethylcellulose;

said lubricant is one or more selected from the group consisting of colloidal silica, sodium stearyl fumarate, talc and magnesium stearate;

said water-soluble hot-melt material is one or more selected from the group consisting of polyethylene glycol 4000-10000, poloxamer, and polyoxyl(40) stearate;

an amount of said water-soluble hot-melt material is 8-25 mass % based on the total mass of said tablet or based on the total mass of the content of the capsule;

the sum of the amount of said filler and said water-soluble carrier is 60-90 mass % based on the total mass of said tablet or the total mass of the content of the capsule;

the amount of said disintegrant is 2-5 mass % based on the total mass of said tablet or the total mass of the content of the capsule; and the amount of said lubricant is 0.5-3 mass % based on the total mass of said tablet or the total mass of the content of the capsule.

25. The method according to claim 24, wherein:

said adjuvants further comprise an antioxidant and/or one or more other adjuvant selected from the group consisting of povidone, hydroxypropyl methylcellulose, sodium lauryl sulfate, poloxamer, polyoxyethylated castor oil, and Tween-80;

an amount of said other adjuvant is no more than 3 mass % based on the total mass of said tablet or the total mass of the content of the capsule; and an amount of said antioxidant is 0.1-10 mass % relative to a mass of the aripiprazole.

26. The method according to claim 25, wherein said antioxidant is one or more selected from the group consisting of sodium metabisulfite, sodium bisulfite, sodium sulfite, sodium thiosulfate, L-cysteine, sodium L-ascorbate, and vitamin C.

* * * * *